US012779204B2

(12) United States Patent
Cezo et al.

(10) Patent No.: US 12,779,204 B2
(45) Date of Patent: Nov. 3, 2026

(54) FLUID DELIVERY BASED INTRAVASCULAR REPERFUSION THERAPY DEVICES, SYSTEMS, AND METHODS

(71) Applicant: KONINKLIJKE PHILIPS N.V., Eindhoven (NL)

(72) Inventors: James David Cezo, Colorado Springs, CO (US); Arjen Van Der Horst, Tilburg (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 193 days.

(21) Appl. No.: 18/693,622

(22) PCT Filed: Sep. 14, 2022

(86) PCT No.: PCT/EP2022/075476
§ 371 (c)(1),
(2) Date: Mar. 20, 2024

(87) PCT Pub. No.: WO2023/046541
PCT Pub. Date: Mar. 30, 2023

(65) Prior Publication Data

US 2024/0424284 A1 Dec. 26, 2024

Related U.S. Application Data

(60) Provisional application No. 63/246,929, filed on Sep. 22, 2021.

(51) Int. Cl.
*A61M 60/523* (2021.01)
*A61M 60/104* (2021.01)
(Continued)

(52) U.S. Cl.
CPC ........ *A61M 60/523* (2021.01); *A61M 60/104* (2021.01); *A61M 60/32* (2021.01);
(Continued)

(58) Field of Classification Search
CPC ........ A61M 1/3613; A61M 2202/0007; A61M 2202/0413; A61M 2202/0468;
(Continued)

(56) References Cited

U.S. PATENT DOCUMENTS 4,459,977 A 7/1984 Pizon
5,533,957 A 7/1996 Aldea
(Continued)

FOREIGN PATENT DOCUMENTS

WO 2023046455 A1 3/2023
WO 2023046501 A1 3/2023
(Continued)

OTHER PUBLICATIONS

International Search Report and Written Opinion of PCT/2022/075476, dated Jan. 19, 2023.

*Primary Examiner* — Amanda K Hulbert

(57) ABSTRACT

A system includes an intravascular reperfusion therapy device configured to be positioned within a coronary vein of a patient to deliver reperfusion therapy to a myocardium of a heart associated with the coronary vein. The intravascular reperfusion therapy device includes a sensor, a pump, and a catheter with a lumen. The intravascular reperfusion therapy device is configured to, using the pump, direct flow of a fluid through the lumen to deliver the reperfusion therapy. The system includes a processor circuit configured to receive, from the sensor, physiological data associated with blood flow through the coronary vein, determine, based on the physiological data, a progression of the reperfusion therapy; and control, based on the progression of the reperfusion therapy, the flow of the fluid through the lumen such that the reperfusion therapy is controlled.

19 Claims, 14 Drawing Sheets

(51) Int. Cl.
*A61M 60/32* (2021.01)
*A61M 60/531* (2021.01)

(52) U.S. Cl.
CPC ... *A61M 60/531* (2021.01); *A61M 2202/0007* (2013.01); *A61M 2202/0413* (2013.01); *A61M 2202/0468* (2013.01); *A61M 2205/10* (2013.01); *A61M 2205/3303* (2013.01); *A61M 2205/3327* (2013.01); *A61M 2205/3334* (2013.01); *A61M 2205/3344* (2013.01); *A61M 2205/3368* (2013.01); *A61M 2205/502* (2013.01); *A61M 2205/583* (2013.01); *A61M 2206/10* (2013.01); *A61M 2210/125* (2013.01); *A61M 2230/005* (2013.01); *A61M 2230/20* (2013.01)

(58) Field of Classification Search
CPC ...... A61M 2205/10; A61M 2205/3303; A61M 2205/3327; A61M 2205/3334; A61M 2205/3344; A61M 2205/3368; A61M 2205/502; A61M 2205/583; A61M 2206/10; A61M 2210/125; A61M 2230/005; A61M 2230/20; A61M 60/104; A61M 60/109; A61M 60/143; A61M 60/216; A61M 60/258; A61M 60/268; A61M 60/32; A61M 60/515; A61M 60/523; A61M 60/531
See application file for complete search history.

(56) References Cited

U.S. PATENT DOCUMENTS

| | | | | |
|---|---|---|---|---|
| 2001/0027287 | A1* | 10/2001 | Shmulewitz ........ | A61M 60/865 604/7 |
| 2003/0044315 | A1 | 3/2003 | Boekstgers | |
| 2009/0171137 | A1* | 7/2009 | Farnan ................ | A61M 60/878 600/16 |
| 2011/0092951 | A1 | 4/2011 | Vaisnys | |
| 2016/0073972 | A1 | 3/2016 | Alpert | |

FOREIGN PATENT DOCUMENTS

| | | | |
|---|---|---|---|
| WO | 2023046608 | A2 | 3/2023 |
| WO | 2023046651 | A2 | 3/2023 |

* cited by examiner

FLUID DELIVERY BASED INTRAVASCULAR REPERFUSION THERAPY DEVICES, SYSTEMS, AND METHODS

TECHNICAL FIELD

The present disclosure relates generally to delivery of a reperfusion therapy, and, in particular, to delivery and control of the reperfusion therapy based on intravascular sensing and via intravascular delivery of fluid. More specifically, physiological data representative of blood flow through a vessel may be used to determine a progression of a reperfusion therapy targeting an area of a heart of a patient, and intravascular delivery of fluid to affect the reperfusion therapy may be controlled based on the determined progression.

BACKGROUND

A percutaneous coronary intervention (PCI) may be utilized to treat a blockage (e.g., an occlusion, a lesion, a stenosis, and/or the like) within a blood vessel. The PCI may include a therapeutic procedure, such as administration of a drug, angioplasty, placement of a stent, and/or the like, that reduces a size of the blockage or opens (e.g., widens) the lumen of the affected blood vessel. To that end, PCI can restore blood flow through a blood vessel and to tissue that receives blood/oxygen via the blood vessel. Moreover, before a PCI therapy is delivered, the reduction in blood flow caused by a blockage within a blood vessel may cause tissue that receives blood/oxygen from the vessel to experience ischemia. Accordingly, PCI may restore or increase blood flow to tissue that experienced ischemia, which may restore the health of the tissue. However, even after a PCI therapy is delivered, blood/oxygen may not always suitably re-perfuse through tissue that has experienced ischemia. In particular, the increase and/or reintroduction of blood flow through the ischemic tissue may trigger an inflammatory response and/or oxidative damage, known as reperfusion injury, along with or in place of restoration of normal function of the tissue.

SUMMARY

Disclosed herein are devices, systems, and methods configured to evaluate (e.g., assess) and control (e.g., modify) progress of a reperfusion therapy targeting an area of a patient's body, such as a portion of the myocardium of the heart of the patient. The system may include an intravascular reperfusion therapy device and a processing system, which may include a processor circuit. The intravascular reperfusion therapy device may be positioned within a blood vessel, such as a coronary vein, of the patient and may deliver the reperfusion therapy to the area, such as myocardium, associated with (e.g., receiving blood flow from or providing blood flow to) the blood vessel. The intravascular reperfusion therapy device may include a sensor, a pump, and a catheter with a lumen and may deliver the reperfusion therapy by directing flow of a fluid through the lumen using the pump. In particular, by using the pump to deliver fluid (e.g., having retrograde flow with respect to the blood flow in the vein) to the coronary vein, the intravascular reperfusion therapy device may generate a back pressure within the coronary vein and may thus deliver reperfusion therapy to the myocardium. Further, the sensor (e.g., a sensing component), may sense physiological data (e.g., flow data, pressure data, and/or the like) representative of blood flow through the blood vessel. In that regard, the physiological data may indicate an effect of the reperfusion therapy on the area. To that end, the processing system may receive the physiological data from the sensor and may determine a progression of the reperfusion therapy delivered to the area. Moreover, based on the progression of the reperfusion therapy, the processing system may control (e.g., modify or maintain) the reperfusion therapy delivered by the intravascular device. In particular, the processing system may control the flow of fluid through the lumen (e.g., pumped through the lumen) of the intravascular reperfusion therapy device and the resulting generated back pressure and delivery of the reperfusion therapy. In this way, the processing system may use a feedback loop with the sensor to adaptively monitor and control delivery of the reperfusion therapy via the intravascular delivery and/or control of fluid flow. In cases where the intravascular reperfusion therapy device is positioned within a coronary vein, for example, when a determined progression of the reperfusion therapy indicates that blood flow to the targeted area is improving and/or that the reperfusion therapy has achieved a particular outcome, the processing system may control the intravascular reperfusion therapy device to gradually decrease the delivery of fluid to the coronary vein and/or to complete (e.g., terminate) the administration of the reperfusion therapy.

In an exemplary aspect, a system is provided. The system includes an intravascular reperfusion therapy device configured to be positioned within a coronary vein of a patient to deliver reperfusion therapy to a myocardium of a heart of the patient associated with the coronary vein, wherein the intravascular reperfusion therapy device comprises a sensor, a pump, and a catheter comprising a lumen, wherein the intravascular reperfusion therapy device is configured to, using the pump, direct flow of a fluid through the lumen to deliver the reperfusion therapy; and a processor circuit in communication with the intravascular reperfusion therapy device and configured to: receive, from the sensor, physiological data associated with blood flow through the coronary vein; determine, based on the physiological data, a progression of the reperfusion therapy delivered to the myocardium of the heart; and control, based on the progression of the reperfusion therapy, the flow of the fluid through the lumen such that the reperfusion therapy is controlled.

In some aspects, to control the flow of the fluid through the lumen, the processor circuit is configured to: control, via the pump, a flow rate of the flow of the fluid through the lumen. In some aspects, to control the flow of the fluid through the lumen, the processor circuit is configured to: control, via the pump, a direction of the flow of the fluid through the lumen. In some aspects, to control the direction of the flow of the fluid through the lumen, the processor circuit is configured to control the intravascular reperfusion therapy device to, using the pump: deliver the fluid from the lumen to the coronary vein to generate a back pressure in a first direction, wherein the first direction is opposite a second direction of the blood flow through the coronary vein; or receive the fluid from the coronary vein via the lumen to reduce a pressure in the coronary vein. In some aspects, to control the flow of the fluid through the lumen, the processor circuit is configured to: control the intravascular reperfusion therapy device to, using the pump, oscillate a direction of the flow of the fluid through the lumen between a first direction and a different, second direction. In some aspects, the intravascular reperfusion therapy device is further configured to control a temperature of the fluid to deliver the reperfusion therapy, In some aspects, based on the progression of the reperfusion therapy, the processor circuit is further configured to: control the intravascular reperfusion therapy device to control the temperature of the fluid such that temperature of the myocardium is controlled. In some aspects, the intravascular reperfusion therapy device is further configured to control an oxygen saturation level in the fluid to deliver the reperfusion therapy, and, based on the progression of the reperfusion therapy, the processor circuit is further configured to: control the intravascular reperfusion therapy device to control the oxygen saturation level in the fluid. In some aspects, the pump is coupled to the catheter and is configured to be positioned within a blood vessel of the patient. In some aspects, the intravascular reperfusion therapy device comprises a first port proximal of the pump and a second port distal of the pump, wherein the first port, the second port, and the pump are in fluid communication with the lumen. In some aspects, to direct the flow of the fluid through the lumen, the intravascular reperfusion therapy device is configured to control the pump to: intake the fluid via the first port and output the fluid via the second port such that the fluid flows through the lumen in a first direction; or intake the fluid via the second port and output the fluid via the first port such that the fluid flows through the lumen in a different, second direction. In some aspects, the pump is positioned external to the patient. In some aspects, the sensor is positioned at a distal portion of the catheter. In some aspects, the intravascular reperfusion therapy device comprises an additional sensor, wherein the processor circuit is further configured to: receive, from the additional sensor, additional physiological data associated with blood flow through the coronary vein, and the processor circuit is configured to determine the progression of the reperfusion therapy further based on the additional physiological data. In some aspects, the fluid comprises at least one of saline or blood. In some aspects, the processor circuit is further configured to: output, to display in communication with the processor circuit, a visual representation of the progression of the reperfusion therapy. In some aspects, the sensor comprises a flow sensor, and the physiological data comprises a blood flow rate. In some aspects, the sensor comprises a pressure sensor, and the physiological data comprises pressure data.

In an exemplary aspect, a system is provided. The system includes an intravascular reperfusion therapy device configured to be positioned within a coronary vein of a patient to deliver reperfusion therapy to a myocardium of a heart of the patient associated with the coronary vein, wherein the intravascular reperfusion therapy device comprises: a catheter comprising a lumen; a flow sensor positioned at a distal portion of the catheter; and a pump in fluid communication with the lumen, wherein the intravascular reperfusion therapy device is configured to deliver the reperfusion therapy by, using the pump, directing flow of a fluid through the lumen to the coronary vein in a first direction to generate back pressure in an opposite, second direction within the coronary vein; and a processor circuit in communication with the intravascular reperfusion therapy device and configured to: receive, from the flow sensor, flow data associated with blood flow through the coronary vein; determine, based on the flow data, a progression of the reperfusion therapy delivered to the myocardium of the heart; and control, based on the progression of the reperfusion therapy, the flow of the fluid through the lumen such that the back pressure within the coronary vein is controlled.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which.

DETAILED DESCRIPTION

Figure 1:
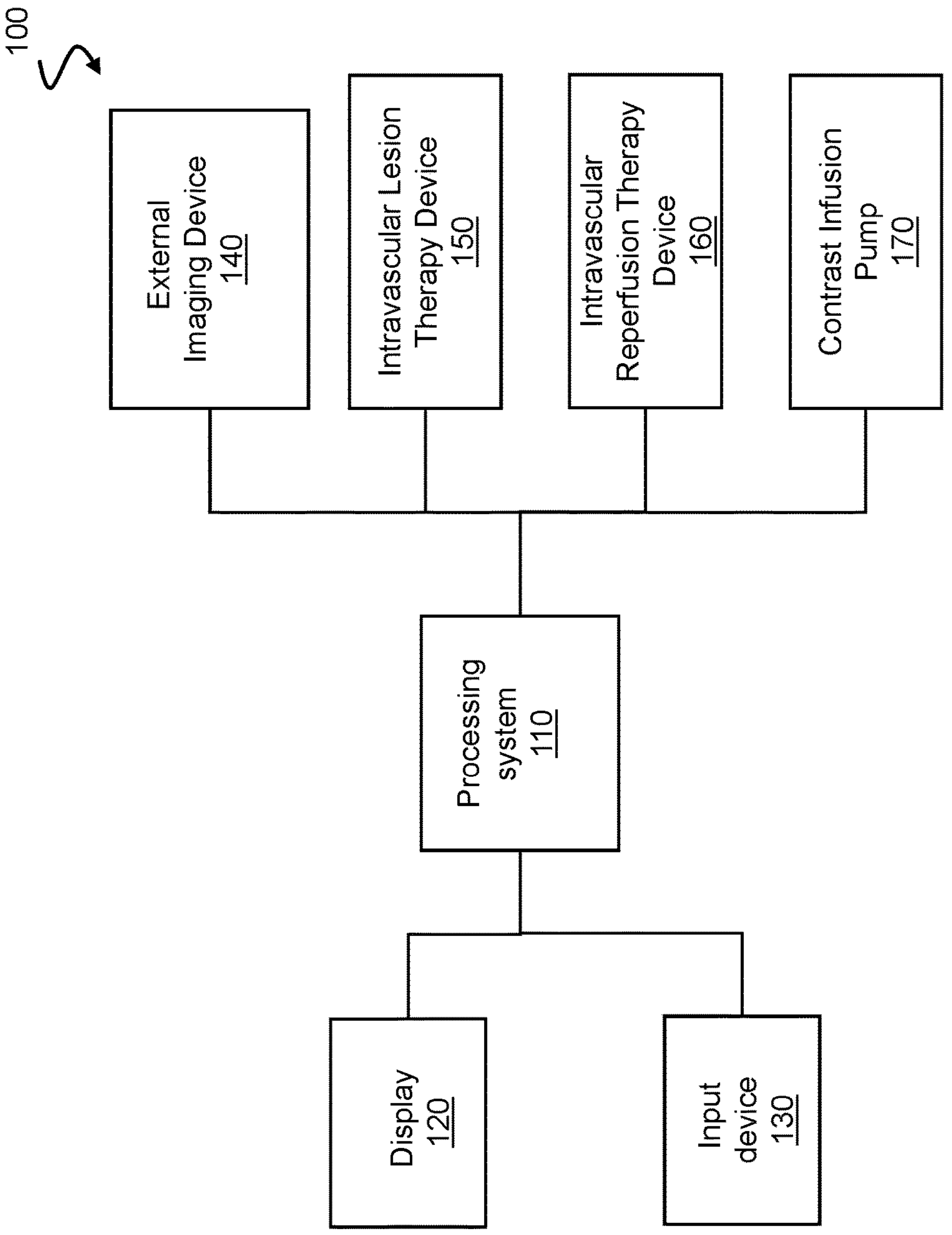
FIG. 1 is a diagrammatic, schematic view of a system, in accordance with at least one embodiment of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. Additionally, while the description below may refer to blood vessels, it will be understood that the present disclosure is not limited to such applications. For example, the devices, systems, and methods described herein may be used in any body chamber or body lumen, including an esophagus, veins, arteries, intestines, ventricles, atria, or any other body lumen and/or chamber. For the sake of brevity, however, the numerous iterations of these combinations will not be described separately.

Aspects of the present disclosure can include features described in App. No. 63/246,946, filed Sep. 22, 2021, App. No. 63/246,904, filed Sep. 22, 2021, App. No. 63/246,963, filed Sep. 22, 2021, and App. No. 63/246,919, filed Sep. 22, 2021, the entireties of which are incorporated by reference herein.

Referring to FIG. 1, shown therein is a system 100 according to an embodiment of the present disclosure. The system 100 can be configured to evaluate (e.g., assess), display, and/or control (e.g., modify) a progress of a reperfusion therapy targeting an area of a patient's body, such as a portion of the myocardium. For instance, the system 100 may be utilized to monitor and/or control reperfusion therapy such that injury to the myocardium following a percutaneous coronary intervention (PCI) is avoided or minimized, as described in greater detail below. In this regard, the system 100 may be used to assess coronary vessels and/or heart tissue (e.g., the myocardium) oxygenated by the coronary vessels. As illustrated, the system 100 includes a processing system 110 in communication with a display 120 (e.g., an electronic display), an input device 130 (e.g., a user input device), an external imaging device 140, an intravascular lesion therapy device 150 (e.g., intraluminal therapy device), an intravascular reperfusion therapy device 160 (e.g., intraluminal reperfusion therapy device), and a contrast infusion pump 170.

The processing system 110 is generally representative of any device suitable for performing the processing and analysis techniques disclosed herein. In some embodiments, the processing system 110 includes processor circuit, such as the processor circuit 200 of FIG. 2. In some embodiments, the processing system 110 is programmed to execute steps associated with the data acquisition, analysis, and/or instrument (e.g., device) control described herein. Accordingly, it is understood that any steps related to data acquisition, data processing, instrument control, and/or other processing or control aspects of the present disclosure may be implemented by the processor circuit (e.g., computing device) using corresponding instructions stored on or in a non-transitory computer readable medium accessible by the computing device. In some instances, the processing system 110 is a console device. Further, it is understood that in some instances the processing system 110 comprises one or a plurality of computing devices, such as computers, with one or a plurality of processor circuits. In that regard, it is particularly understood that the different processing and/or control aspects of the present disclosure may be implemented separately or within predefined groupings using a plurality of computing devices. Any divisions and/or combinations of the processing and/or control aspects described below across multiple computing devices are within the scope of the present disclosure.

Figure 2:
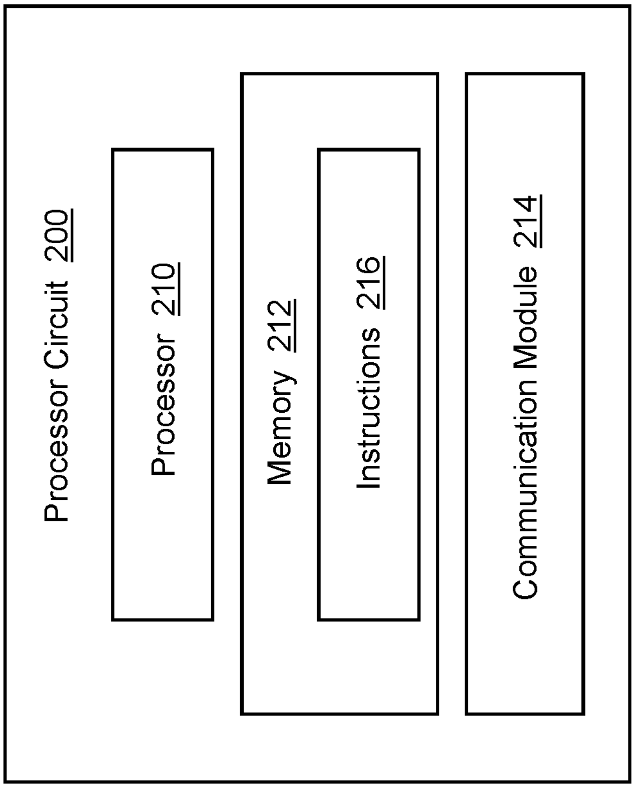
FIG. 2 is a schematic diagram of a processor circuit, in accordance with at least one embodiment of the present disclosure.

FIG. 2 is a schematic diagram of a processor circuit 200, according to embodiments of the present disclosure. The processor circuit 200 may be implemented in the processing system 110 of FIG. 1. As shown, the processor circuit 200 may include a processor 210, a memory 212, and a communication module 214. These elements may be in direct or indirect communication with each other, for example via one or more buses.

The processor 210 may include a central processing unit (CPU), a digital signal processor (DSP), an ASIC, a controller, an FPGA, another hardware device, a firmware device, or any combination thereof configured to perform the operations described herein. The processor 210 may also be implemented as a combination of computing devices, e.g., a combination of a DSP and a microprocessor, a plurality of microprocessors, one or more microprocessors in conjunction with a DSP core, or any other such configuration.

The memory 212 may include a cache memory (e.g., a cache memory of the processor 210), random access memory (RAM), magnetoresistive RAM (MRAM), read-only memory (ROM), programmable read-only memory (PROM), erasable programmable read only memory (EPROM), electrically erasable programmable read only memory (EEPROM), flash memory, solid state memory device, hard disk drives, other forms of volatile and non-volatile memory, or a combination of different types of memory. In an embodiment, the memory 212 includes a non-transitory computer-readable medium. The memory 212 may store instructions 216. The instructions 216 may include instructions that, when executed by the processor 210, cause the processor 210 to perform the operations described herein with reference to the processing system 110 (FIG. 1). Instructions 216 may also be referred to as code. The terms "instructions" and "code" should be interpreted broadly to include any type of computer-readable statement(s). For example, the terms "instructions" and "code" may refer to one or more programs, routines, sub-routines, functions, procedures, etc. "Instructions" and "code" may include a single computer-readable statement or many computer-readable statements.

The communication module 214 can include any electronic circuitry and/or logic circuitry to facilitate direct or indirect communication of data between various components of the processor circuit 200 and/or the processing system 110 (FIG. 1). Additionally or alternatively, the communication module 214 can facilitate communication of data between the processor circuit 200, the display 120 (e.g., a monitor), the input device 130, the external imaging device 140, the intravascular lesion therapy device 150, the intravascular reperfusion therapy device 160, the contrast infusion pump 170, and/or the like. In that regard, the communication module 214 can be an input/output (I/O) device interface, which may facilitate communicative coupling between the processor circuit 200 and (I/O) devices, such as the input device 130. Moreover, the communication module 214 may facilitate wireless and/or wired communication between various elements of the processor circuit 200 and/or the devices and systems of the system 100 using any suitable communication technology, such as a cable interface such as a USB, micro USB, Lightning, or FireWire interface, Bluetooth, Wi-Fi, ZigBee, Li-Fi, or cellular data connections such as 2G/GSM, 3G/UMTS, 4G/LTE/WiMax, or 5G.

Turning back now to FIG. 1, the external imaging device 140 can include an x-ray system, angiography system, fluoroscopy system, ultrasound system, computed tomography (CT) system, a magnetic resonance imaging (MRI) system, other suitable imaging devices, and/or combinations thereof. The external imaging device 140 may additionally or alternatively include a nuclear medicine imaging device, such as a gamma camera or a single-photon emission computed tomography (SPECT) system, other suitable devices, and/or combinations thereof. The external imaging device 140 can be configured to acquire imaging data of anatomy, such as the heart and blood vessels, while the external imaging device 140 is positioned outside of the body of the patient. The imaging data can be visualized in the form of two-dimensional and/or three-dimensional images of the heart, blood vessel, and/or other anatomy. In some embodiments, the imaging device 140 need not be an external device that is positioned outside the patient body. For example, the imaging device 140 can be an intracardiac echocardiography (ICE) catheter that obtains images while positioned within a heart chamber. In some embodiments, the imaging device 140 may be an external device in that is it is positioned outside of the particular anatomy that is being imaged (e.g., blood vessels and/or heart), but is positioned inside the patient body. For example, the imaging device 140 can be a transesophageal echocardiography (TEE) probe that obtains images while positioned within an esophagus.

Moreover, the external imaging device 140 may obtain images of the heart that are indicative of the health of the cardiac muscle or myocardium. In particular, the external imaging device 140 can be configured to acquire imaging data that illustrates myocardial perfusion (e.g., myocardial perfusion imaging (MPI) data). For example, MPI data can be collected by imaging a radiopharmaceutical agent, such as thallium, in the patient's heart muscle using a SPECT system. Additionally or alternatively, the imaging data may be obtained by imaging a contrast agent, which may be administered to the patient's vasculature manually or via the contrast infusion pump 170, for example. In any case, the imaging data can illustrate vasculature and/or muscle mass with blood flow and/or vasculature and/or muscle mass that lack of blood flow in areas of the heart.

The contrast infusion pump 170 may administer a contrast agent, which may alter an appearance (e.g., a brightness, an intensity, a contrast) of a feature within an external imaging data, such as the external imaging data obtained by the external imaging device 140. In that regard, the contrast infusion pump 170 may be configured to administer, to the patient, a contrast agent that is radiopaque and enhances the visibility of internal fluids or structures within a patient's anatomy. In some embodiments, for example, the contrast agent absorbs external x-rays from an x-ray source, resulting in decreased exposure on an x-ray detector in conjunction with the x-ray source. The contrast agent may be of any suitable material, chemical, or compound and, before administration to the patient, may be a liquid, powder, paste, tablet, or of any other suitable form. For example, the contrast agent may include iodine-based compounds, barium sulfate compounds, gadolinium-based compounds, microbubbles, or any other suitable compounds, which may be included in a solution or suspension, for example, for administration to the patient. In some embodiments, the contrast agent may include carbon dioxide, which may be a gas. In such cases, the contrast agent may decrease absorption of the external x-rays from the x-ray source, when administered. The contrast agent may additionally be referred to as a radiocontrast agent, a contrast dye, a radiocontrast dye, a contrast material, a radiocontrast material, a contrast media, or a radiocontrast media, among other terms. Further, in some embodiments, the contrast infusion pump 170 may be configured to combine or switch between different contrast agents, which may reduce stress on the patient's body. For instance, the contrast infusion pump 170 may administer a first contrast agent for a period of time and may subsequently administer a different, second contrast agent to the patient during an imaging procedure.

The intravascular lesion therapy device 150 may be any form of device, instrument, or probe sized and shaped to be positioned within a vessel. For example, the intravascular lesion therapy device 150 is generally representative of a guide wire, a catheter, or a guide catheter. However, in other embodiments, the intravascular lesion therapy device 150 may take other forms. In that regard, the intravascular lesion therapy device 150 may be a device configured to deliver a PCI therapy to a vessel. In particular, the intravascular lesion therapy device 150 may be an intravascular guidewire or catheter configured to ablate a lesion (e.g., a blockage) within the vessel, deploy a balloon, a stent, and/or drug to a target site within the vessel, and/or the like. That is, for example, the intravascular lesion therapy device 150 may be a stent or balloon delivery device (e.g., an angioplasty device), a thrombectomy device, an atherectomy device, and/or the like. In that regard, the intravascular lesion therapy device 150 may include a coil retriever, an aspiration (e.g., suction) device, and/or the like to assist in the removal of a clot or occlusion from the patient's vessel. In some embodiments, the intravascular lesion therapy device 150 may include a laser, a blade (e.g., knife), a sanding crown, and/or any suitable device that may assist in the cutting, shaving, sanding, vaporizing, and/or removal of atherosclerotic plaque from the patient's vessel. Additionally or alternatively, the intravascular lesion therapy device 150 may be the therapy itself delivered to the vessel. More specifically, the intravascular lesion therapy device 150 may represent a stent or balloon deployed to the vessel, a drug administered intra or extravascularly (e.g., orally), and/or the like. To that end, while the intravascular lesion therapy device 150 is illustrated as being communicatively coupled to the processing system 110, embodiments are not limited thereto.

In some embodiments, the intravascular reperfusion therapy device 160 may be a device, instrument, or probe sized and shaped to be positioned within a vessel. In particular, the intravascular reperfusion therapy device 160 may be a device or instrument configured to control reperfusion of blood flow into a target tissue area (e.g., capillary bed), such as a portion of the myocardium of a patient. In some embodiments, the target tissue area may be an ischemic area and/or an area of tissue that receives reduced blood flow due to a blockage in an associated vessel (e.g., an upstream artery). As described in greater detail below, treatment (e.g., therapy) directed to the vessel associated with the blockage, such as treatment via the intravascular lesion therapy device 150, may reintroduce or increase blood flow to the target tissue area. To reduce or prevent injury to the target tissue area resulting from this increased blood flow, the intravascular reperfusion therapy device 160 may be positioned intravascularly, such as within a coronary blood vessel, and may be configured to regulate blood flow to the target tissue. In some embodiments, the reperfusion therapy can include administration of anti-inflammatory drug(s) or nitric oxide (NO) to the patient. In some embodiments, the reperfusion therapy can include cold fluid that is provided via the arterial side.

In some embodiments, one or more of the external imaging device 140, the intravascular lesion therapy device 150, the intravascular reperfusion therapy device 160, and/or the contrast infusion pump 170, are located proximate one or more of the processing system 110, the display device 120, and/or the input device 130, such as in the same procedure room. In some embodiments, one or more of the external imaging device 140, the intravascular lesion therapy device 150, the intravascular reperfusion therapy device 160, and/or the contrast infusion pump 170 are located spaced from one or more of the processing system 110, the display device 120, and/or the input device 130, such as in different procedure rooms or facilities. For example, the external imaging device 140, the intravascular lesion therapy device 150, the intravascular reperfusion therapy device 160, and/or the contrast infusion pump 170 can be part of different systems that are communicatively coupled. In that regard, the processing system 110 can be configured to acquire the data collected from the components spaced therefrom and process the data as described herein. The external imaging device 140, the intravascular lesion therapy device 150, the intravascular reperfusion therapy device 160, and/or the contrast infusion pump 170 can be configured to transmit the collected data to the processing system 110.

The system 100 includes a display device 120 that is communicatively coupled to the processing system 110. In some embodiments, the display device 120 is a component of the processing system 110, while in other embodiments, the display device 120 is distinct from the processing system 110. In some embodiments, the display device 120 is a monitor integrated in a console device or a standalone monitor (e.g., a flat panel or flat screen monitor). The processing system 110 can be configured to generate a visual display (e.g., screen display) based on imaging data from the external imaging device 140. The processing system 110 can provide (e.g., output) the screen display to the display device 120. To that end, the display device 120 may be configured to output (e.g., display) a two-dimensional image and/or a two-dimensional representation of the heart, blood vessels, and/or other anatomy, which may be included in the screen display. In some embodiments, the display device 120 is configured to output a three-dimensional graphical representation of the heart, blood vessels, and/or other anatomy. For instance, the display device 120 may be a holographic display device configured to output a three-dimensional holographic display of anatomy. Any suitable display device is within the scope of this disclosure, including self-contained monitors, projection/screen systems, head-up display systems, etc. The display device can implement principles based on moving reflective microelectromechanical systems (MEMS), laser plasma, electro-holography, etc. In some embodiments, the display device 120 is implemented as a bedside controller having a touch-screen display as described, for example, in U.S. Provisional Application No. 62/049,265, titled "Bedside Controller for Assessment of Vessels and Associated Devices, Systems, and Methods," and filed Sep. 11, 2014, the entirety of which is hereby incorporated by reference herein.

The system 100 includes an input device 130 that is communicatively coupled to the processing system 110. The input device 130 may be a peripheral device, such as a touch sensitive pad, a touch-screen, a joy-stick, a keyboard, mouse, trackball, a microphone, an imaging device, and/or the like. In other embodiments, the user interface device is part of the display device 120, which may be a touch-screen display, for example. Moreover, a user may provide an input to the processing system 110 via the input device 130. In particular, the input device 130 may enable a user to control, via inputs to the processing system 110, one or more of the components of the system 100, such as the external imaging device 140, the intravascular lesion therapy device 150, the intravascular reperfusion therapy device 160, the contrast infusion pump 170, or the processing system 110 itself. Additionally or alternatively, the input device 130 may facilitate interaction with a screen display provided at the display device 120. For instance, a user may select, edit, view, or interact with portions of the screen display (e.g., a GUI) provided at the display device 120 via the input device 130.

The system 100 can include various connectors, cables, interfaces, connections, etc., to communicate between the elements of the intravascular lesion therapy device 150, the intravascular reperfusion therapy device 160, the processing system 110, the external imaging device 140, the display device 120, and/or the input device 130. In some embodiments, for example, the communication module 214 (FIG. 2), which may be included in the processing system 110, may include such connectors, interfaces, and/or the like. In that regard, the processing system 110 can communicate and/or control one or more components of the system 100 via mechanical and/or electromechanical signaling and/or controls. Further, the illustrated communication pathways are exemplary in nature and should not be considered limiting in any way. In that regard, it is understood that any communication pathway between the components of system 100 may be utilized, including physical connections (including electrical, optical, and/or fluid connections), wireless connections, and/or combinations thereof. In that regard, it is understood that the one or more of the components of the system 100 can communicate via a wireless connection in some instances. In some instances, the one or more components of the system 100 and/or other systems (e.g., of a hospital or health services provider) communicate via a communication link over a network (e.g., intranet, internet, telecommunications network, and/or other network).

Figure 3A:
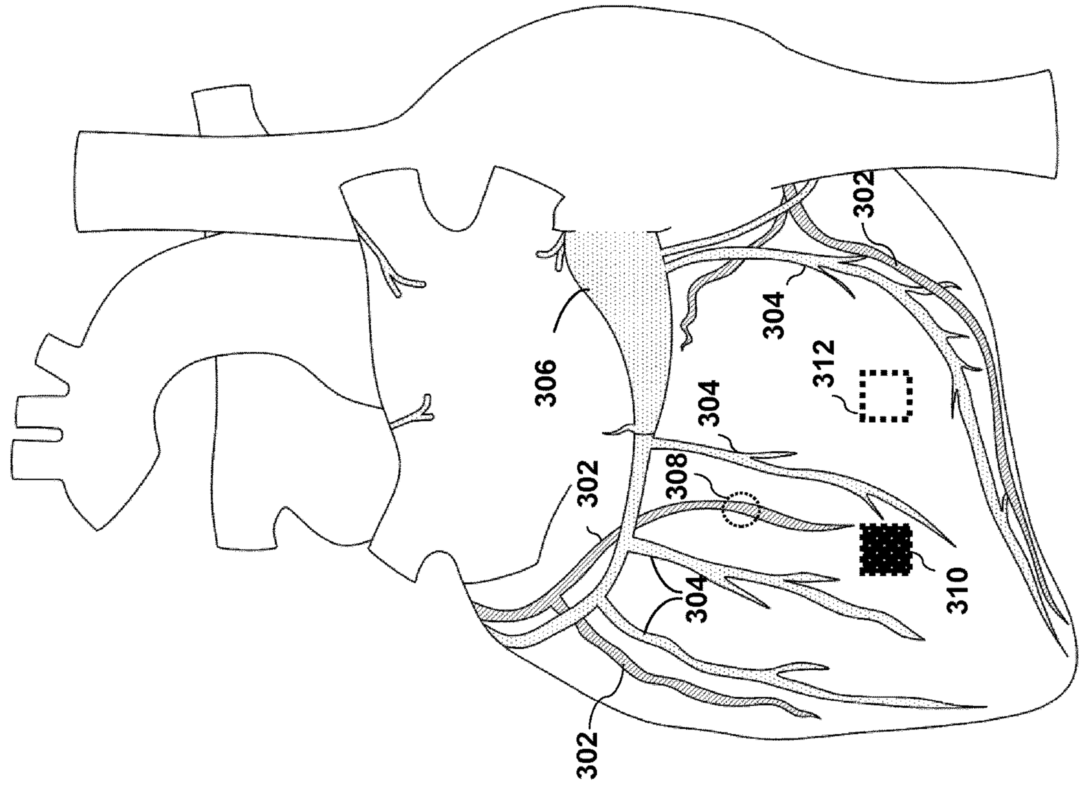
FIG. 3A is diagram of a human heart with an obstruction, in accordance with at least one embodiment of the present disclosure.
Figure 3B:
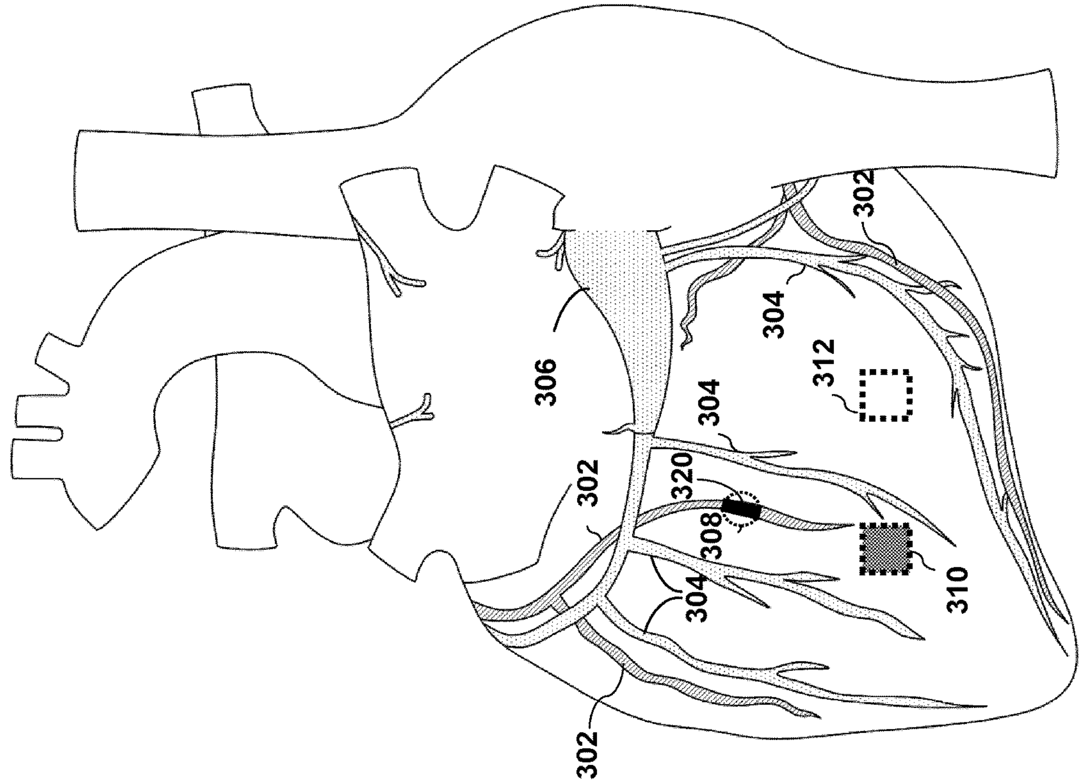
FIG. 3B is diagram of the human heart following a percutaneous coronary intervention (PCI), in accordance with at least one embodiment of the present disclosure.
Figure 3C:
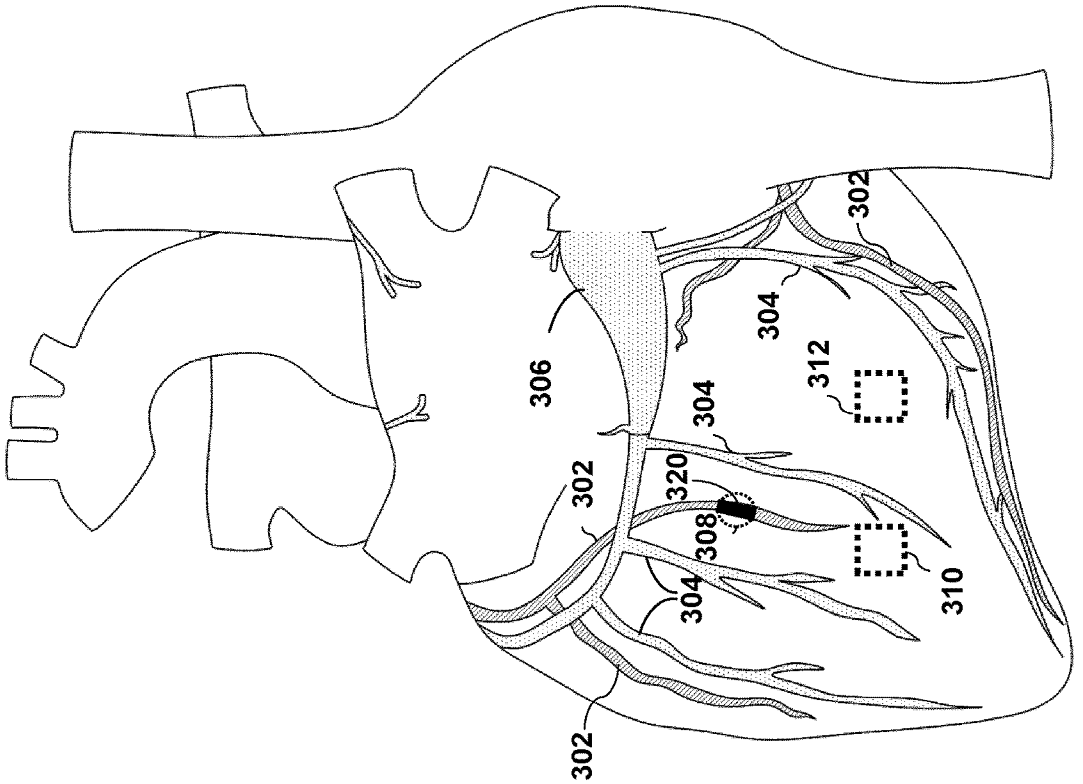
FIG. 3C is diagram of the human heart following a reperfusion therapy, in accordance with at least one embodiment of the present disclosure.

FIGS. 3A-3C illustrate a diagram of a human heart 300. As illustrated, the heart 300 includes coronary arteries 302 (illustrated with a first fill pattern) that deliver oxygenated blood to tissue, such as muscle tissue (e.g., myocardium), of the heart 300. The heart 300 further includes coronary veins 304 (illustrated with a second fill pattern), including a coronary sinus 306, that carry deoxygenated blood away from the tissue of the heart and towards a chamber (e.g., an atrium) of the heart 300.

In the diagram illustrated in FIG. 3A, a coronary artery 302 of the heart 300 includes a blockage 308 (e.g., an occlusion, a lesion, a stenosis, and/or the like). The blockage 308 may disrupt flow through the coronary artery 302. In particular, the blockage 308 may decrease the diameter of a portion of the lumen of the coronary artery 302, which may decrease the flow of blood through the portion of the lumen. As a result, a first area of tissue 310 (e.g., a portion of the myocardium) that is associated with (e.g., receives blood from) the coronary artery 302 with the blockage 308 may not receive a healthy amount of blood/oxygen. For instance, the blood/oxygen delivered to the first area of tissue 310 may not be sufficient to perfuse through (e.g., to be distributed across) the entire first area of tissue 310 in some cases. In this regard, the first area of tissue 310 may experience ischemia (e.g., a reduction in delivered blood/oxygen illustrated by a relatively dark fill pattern), which may damage the first area of tissue 310. In some embodiments, the first area 310 can be and/or include coronary artery 302 with the blockage. In some embodiments, the first area of the heart may be vasculature and/or tissue associated with (e.g., receiving blood flow from) a first vessel with a previous blockage (as opposed to a current blockage). In some embodiments, the first area may be an area that experiences or has experienced a period of reduced blood flow/ischemia. The illustrated different, second area of tissue 312 (e.g., a portion of the myocardium) may receive blood/oxygen from a different coronary artery 302 than the first area of tissue 310. In this regard, the second area of tissue 312 may remain relatively unaffected by the blockage 308. To that end, the second area of tissue 312 may receive a healthy amount of blood/oxygen, and the second area of tissue 312 may not experience ischemia. Accordingly, the second area of tissue 312 is illustrated as being healthy by a lack of the fill pattern (e.g., by a relatively brighter and/or whiter fill) shown in the first area of tissue 310. In some embodiments, the second area 312 can be and/or include coronary artery 302 without the blockage.

In some embodiments, a percutaneous coronary intervention (PCI) may be utilized to treat the blockage 308. In particular, the PCI may include a therapeutic procedure that reduces a size of the blockage 308, opens (e.g., widens) the lumen of a vessel, and/or the like to restore blood flow through the vessel (e.g., the coronary artery 302) with the blockage 308. In that regard, the PCI may include, for example, angioplasty (e.g., deploying a balloon) and positioning a stent across the stenosis to open the vessel (e.g., the coronary artery 302 with the blockage). The PCI may additionally or alternatively include thrombectomy, atherectomy, administration of a drug and/or the like. To that end, the intravascular lesion therapy device 150 (FIG. 1) may facilitate and/or provide the PCI to a vessel having a blockage (e.g., blockage 308).

FIG. 3B illustrates a diagram of the heart 300 after delivery of a therapeutic procedure (e.g., post-treatment), such as PCI. In particular, FIG. 3B illustrates a stent 320 positioned within the coronary vessel at the site of the blockage 308. However, embodiments are not limited thereto. In that regard, the PCI delivered to the coronary artery 302 or a vessel with a blockage may include any suitable combination of the therapies described above.

As described above, the stent 320 and/or another suitable PCI (e.g., therapeutic procedure) may be provided to a vessel so that an effect of a blockage on blood flow through the vessel is reduced. In this regard, the placement of the stent 320 within the coronary artery 302 (e.g., at the site of the blockage 308) may open (e.g., widen) the portion of the lumen of the coronary artery 302 with the blockage 308, which may increase blood flow through the portion lumen. Moreover, the placement of the stent 320 within the heart 300 may increase blood flow downstream of the blockage 308, such as within vasculature that receives blood flow from the portion of the lumen. In this way, the vasculature (e.g., a capillary bed) that delivers blood/oxygen to the first area of tissue 310 may receive increased blood flow, which may increase blood/oxygen delivery to the first area of the tissue 310. To that end, blood/oxygen may re-perfuse the first area of the tissue 310. Accordingly, the stent 320 may reverse or reduce the ischemia experienced by the first area of the tissue 310. In this regard, the first area of the tissue 310 is illustrated in FIG. 3B with a different fill pattern (e.g., a relatively brighter and/or lighter fill pattern) than the fill pattern illustrated in FIG. 3A to demonstrate the increased blood/oxygen supplied to the first area of the tissue 310.

In some cases, blood/oxygen may not suitably perfuse through tissue associated with an occluded vessel (e.g., a vessel with a blockage), such as the first area of tissue 310, after delivery of a PCI therapy. For example, in some cases, the introduction and/or increase of blood flow to tissue that has experienced ischemia may result in reperfusion injury (e.g., ischemia-reperfusion injury). In particular, the returned blood flow may trigger an inflammatory response and/or oxidative damage along with or in place of restoration of normal function of the tissue. Inflammation, damage resulting from inflammation, and/or the oxidative damage may obstruct the flow of blood/oxygen within the tissue (e.g., within a capillary bed associated with the tissue). Accordingly, blood/oxygen may not be distributed throughout (e.g., perfuse through) the tissue at a healthy level even after the delivery of a PCI therapy. For instance, blood may preferentially flow through a first portion of the tissue lacking inflammation and/or damage and may flow through a second portion of the tissue with inflammation and/or damage to a lesser degree. As a result, the second portion of the tissue may continue to receive blood flow below a healthy level. In this regard, the first area of the tissue 310 is illustrated in FIG. 3B with a different fill pattern (e.g., a relatively darker fill pattern) than the second area of the tissue 312 (e.g., a healthy area of tissue) to demonstrate that the stent 320 alone may not fully restore the health and/or functioning of the first area of the tissue 310.

Turning now to FIG. 3C, in some cases, the reperfusion of blood/oxygen within ischemic tissue may be further assisted and/or controlled by reperfusion therapy. To that end, FIG. 3C illustrates a diagram of the heart 300 after delivery of the PCI therapy and a reperfusion therapy, such as a therapy delivered by the intravascular reperfusion therapy device 160. In particular, FIG. 3C illustrates a diagram of the heart 300 following delivery of a reperfusion therapy targeting the first area of tissue 310. According to techniques described in greater detail below, reperfusion therapy may be delivered by the intravascular reperfusion therapy device 160 to reduce or minimize injury at and/or to improve blood flow to tissue where blood is re-perfusing (e.g., an area of tissue receiving an increase in blood flow), such as the first area of tissue 310. In particular, reperfusion therapy may affect a distribution of blood flow through the targeted tissue such that blood flow perfuses (e.g., distributes to) and/or increases throughout the tissue, including through areas of the tissue that are inflamed or have oxidative damage. Accordingly, delivery of the reperfusion therapy targeting an area of tissue may restore blood flow to a healthy amount or an amount exceeding the blood flow resulting from the PCI therapy alone. For instance, in the illustrated embodiment, the health and/or functioning of (e.g., the blood flow to) the first area of tissue 310 is shown as being fully restored by the reperfusion therapy, as indicated by the fill pattern of the first area of tissue 310 matching the second area of tissue 312. In some embodiments, however, the reperfusion therapy may restore the health and/or functioning of (e.g., the blood flow to) tissue to a level greater than a level resulting from the PCI but less than a level at an area of tissue, such as the second area of tissue 312, that was relatively unaffected by a blockage (e.g., associated with a different vessel than the vessel having the blockage). Particular mechanisms for controlling, using one or more components of the system 100, the reperfusion of an area of tissue associated with (e.g., configured to receive blood/oxygen from) a vessel that receives a PCI therapy (e.g., a vessel that has an occlusion) and/or otherwise receives an increase in blood flow are described herein.

Figure 4:
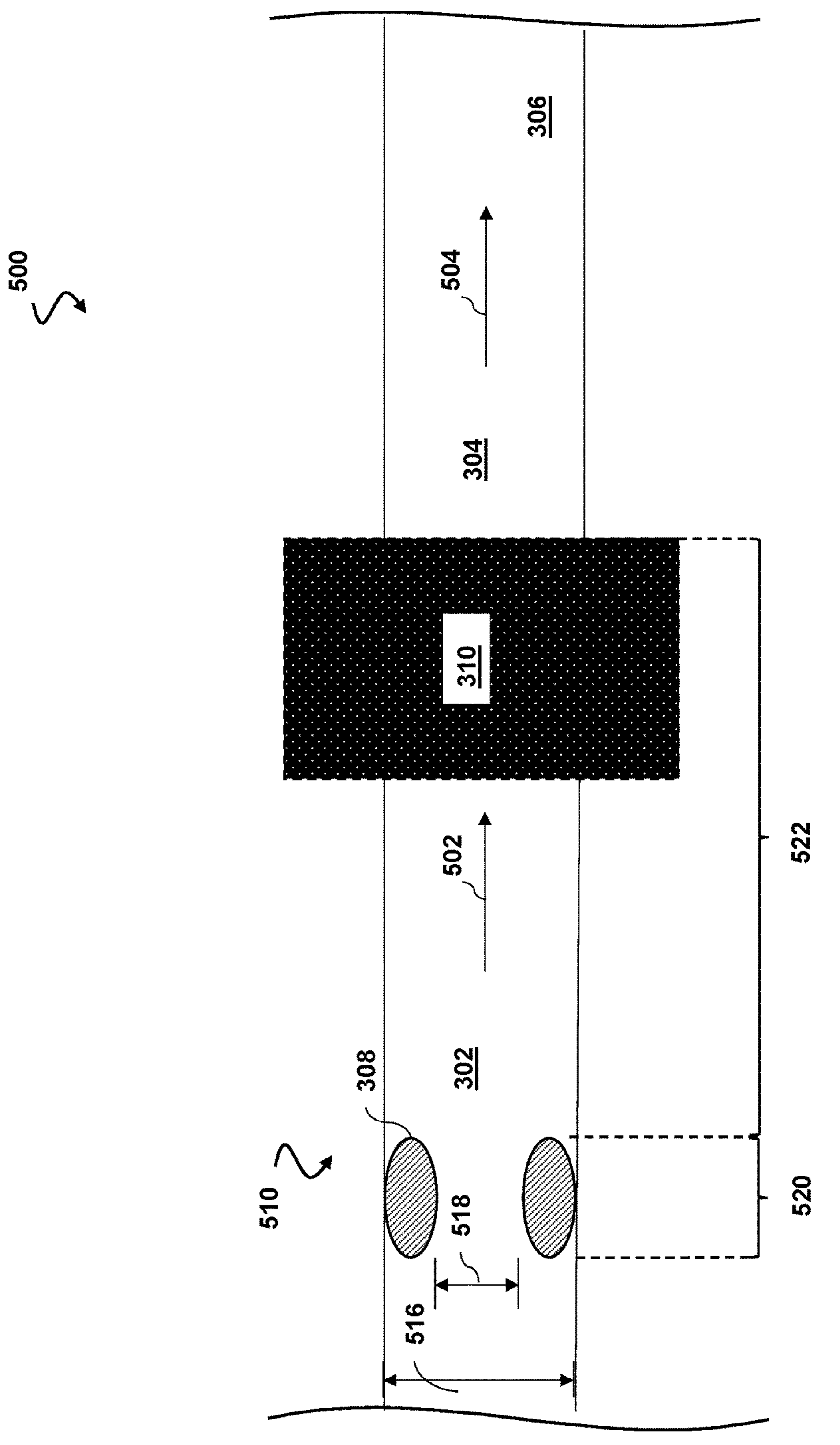
FIG. 4 is a schematic diagram of a portion of a heart, in accordance with at least one embodiment of the present disclosure.

FIG. 4 illustrates a schematic diagram of a portion 500 of a heart of a patient. FIG. 4 may correspond to a detailed view of a portion of the heart 300 illustrated in FIG. 3A. More specifically, FIG. 4 illustrates a coronary artery 302, which includes a blockage 308 (e.g., a stenosis) and is arranged to provide blood/oxygen to an area of tissue 310, as indicated by the arrow 502. A coronary vein 304 is arranged to carry deoxygenated blood away from the area of tissue 310, as indicated by the arrow 504, and is illustrated as being in fluid communication with the coronary sinus 306.

As described above with respect to FIGS. 3A-3B, the blockage 308 may disrupt blood flow through the coronary artery 302. In particular, the blockage 308 may reduce a diameter of a lumen of the coronary artery 302 from a first diameter 516 to a smaller, second diameter 518 within the portion 520 of the vessel where the blockage 308 is located. This reduction in diameter may increase the resistance and/or the impedance to blood flowing through the portion 520, which may reduce blood/oxygen delivered distal of the blockage (e.g., within the distal area 522 including a portion of the coronary artery 302 and the area of tissue 310). In this regard, the area of tissue 310 (e.g., myocardium) may experience ischemia (e.g., a reduction in delivered blood/oxygen), which may damage the area of tissue 310.

Figure 5:
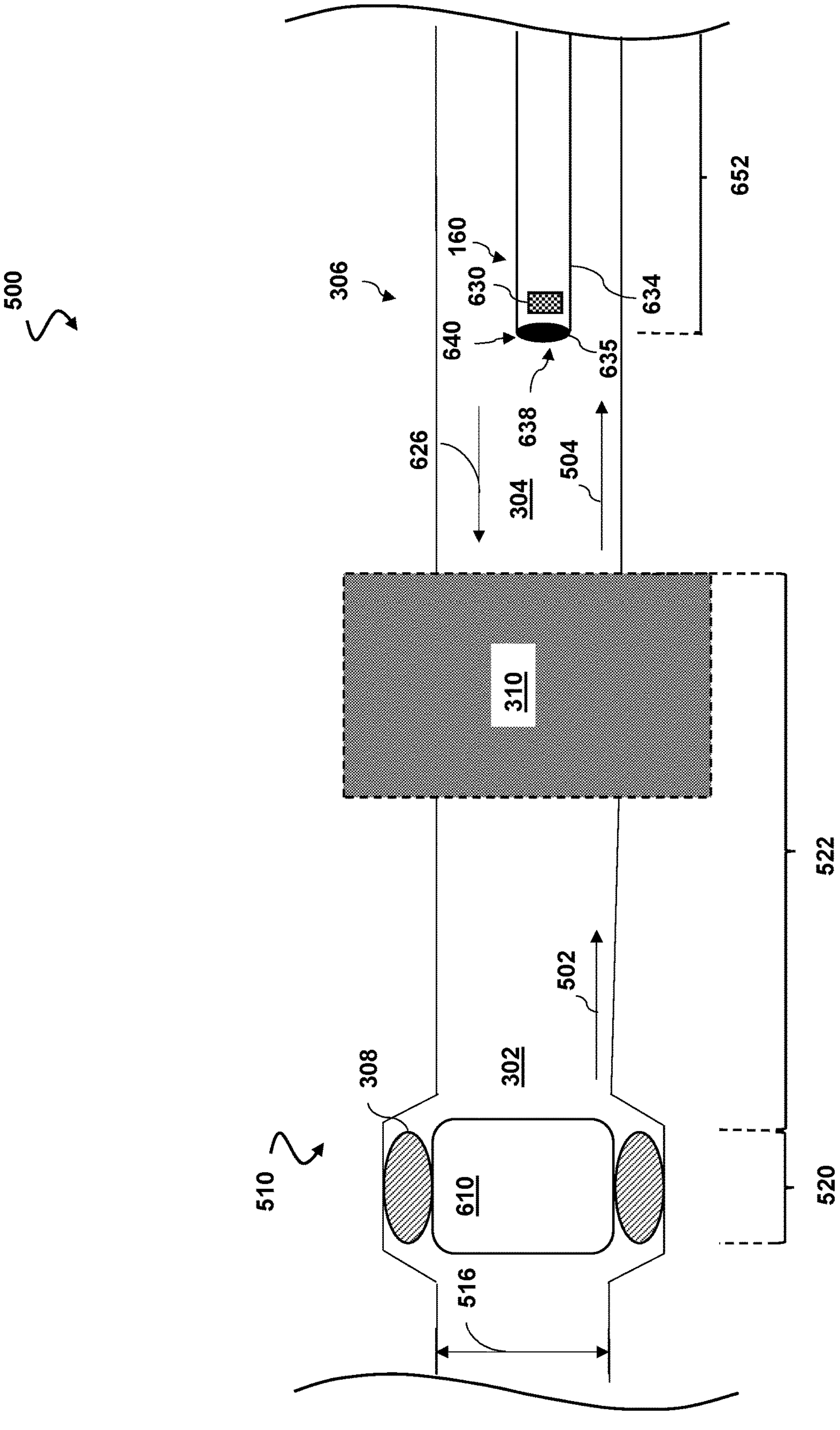
FIG. 5 is a schematic diagram of a portion of a heart, in accordance with at least one embodiment of the present disclosure.

FIG. 5 is a schematic diagram of the portion 500 of the heart during and/or following delivery of a PCI therapy 610 and/or during delivery of a reperfusion therapy. FIG. 5 may correspond to a detailed view of a portion of the heart 300 illustrated in FIG. 3B. The PCI therapy 610 may be delivered by the intravascular lesion therapy device 150 and/or the PCI therapy 610 may be the intravascular lesion therapy device 150 itself. For instance, as described above with respect to FIG. 1, the PCI therapy 610 may involve ablation of the blockage 308, deployment of a balloon (e.g., angioplasty), stent, and/or drug, thrombectomy, atherectomy, and/or the like. In that regard, the PCI therapy 610 may involve a therapeutic procedure that widens the diameter available for blood flow in the portion 520 having the blockage 308 from the diameter 518. That is, for example, the PCI therapy 610 may involve widening the diameter of the lumen of the coronary artery 302, as shown. Additionally or alternatively, a size of the blockage 308 may be reduced (e.g., ablated or removed) to increase the diameter available for blood flow within the portion 520. Further, the PCI therapy 610 may involve the placement of a physical device, such as a stent, within the coronary artery 302. In some embodiments, the PCI therapy 610 may involve the use of a device (e.g., a guidewire or catheter) that is removed from the coronary artery 302 when the PCI therapy 610 is completed. In that regard, the illustrated representation of the PCI therapy 610 positioned within the coronary artery 302 is intended to be exemplary and not limiting.

FIG. 5 further illustrates the intravascular reperfusion therapy device 160, which is shown as including a sensor 630, a catheter 634, and a port 635. The intravascular reperfusion therapy device 160 may deliver reperfusion therapy targeting (e.g., in association with) the area of tissue 310. In particular, the intravascular reperfusion therapy device 160 is shown as being positioned at and delivering reperfusion therapy via a venous side (e.g., within the coronary sinus 306) of the area of tissue 310. In some embodiments, reperfusion therapy delivered to a venous side of the area of tissue 310 may involve the increase of pressure at the venous side of the first area of tissue 310, which may encourage better (e.g., increased and/or more even) distribution of blood flow through the area of tissue 310, especially the damaged or inflamed portions of the area of tissue 310. In that regard, the intravascular reperfusion therapy device 160 is shown as generating a back pressure and/or back flow in a direction, indicated by arrow 626, opposite the direction, indicated by arrow 504, of blood flow through the coronary vein 304. To generate the back pressure and/or back flow (e.g., increase the pressure on the venous side of the area of tissue 310), the intravascular reperfusion therapy device 160 may be configured to supply (e.g., deliver) fluid, such as saline or blood, to the coronary vein 304. For instance, the intravascular reperfusion therapy device 160 may pump fluid into the coronary vein 304 via the port 635. Moreover, as described in greater detail below, control of the flow of fluid through a lumen 638 of the catheter 634 in fluid communication with the port 635 may control the level (e.g., degree) and/or the aggressiveness of reperfusion therapy delivered by the intravascular reperfusion therapy device 160.

As illustrated, the intravascular reperfusion therapy device 160 may include one or more flexible elongate members, such as the catheter 634. In some embodiments, the one or more flexible elongate members may include a guidewire, which may extend through a portion of the catheter 634. In some embodiments, the port 635 may be positioned at a distal portion 652, such as a distal end 640, of the catheter 634. The intravascular reperfusion therapy device 160 may further include one or more sensing components, such as the sensor 630. In some embodiments, the sensor 630 may be positioned at the distal portion 652 of the catheter 634, such as at the distal end 640 of the catheter 634 or spaced from and adjacent to the distal end 640 of the catheter 634. As illustrated and described with respect FIGS. 6 and 7, the intravascular reperfusion therapy device 160 may further include a second sensor 710. Moreover, embodiments of the intravascular reperfusion therapy device 160 are not limited to a single sensor or a pair of sensors. In that regard, the intravascular reperfusion therapy device 160 may include any suitable number (e.g., 1, 2, 3, 5, 10, and/or the like) of sensors, which may be positioned on the catheter 634 or a guidewire of the intravascular reperfusion therapy device 160.

In some embodiments, the one or more sensors (e.g., 630 and 710) of the intravascular reperfusion therapy device 160 may be configured to sense (e.g., obtain) physiological data from within a blood vessel of the patient, such as a coronary vein 304 and/or the coronary sinus 306. In that regard, the physiological data may be associated with blood flow through the blood vessel. For instance, the one or more sensors may obtain flow data associated with a flow rate or flow velocity of blood through the blood vessel (e.g., a blood flow rate or a blood flow velocity, respectively), pressure data associated with a blood pressure within the blood vessel, and/or the like. To that end, the one or more sensors may include a flow sensor configured to obtain the flow data, a pressure sensor configured to obtain the pressure data, and/or the like. In some embodiments, the intravascular reperfusion therapy device 160 may additionally or alternatively include an imaging device configured to obtain intravascular imaging data, such as intravascular ultrasound (IVUS) imaging data, optical coherence tomography (OCT) imaging data, and/or the like. The imaging data may be used to determine pressure data, flow data, and/or characteristics of the blood vessel, such as a diameter of the vessel, which may be useful for determining the pressure and/or flow data. Additionally or alternatively, the intravascular reperfusion therapy device 160 may include a sensor configured to determine and/or monitor a pressure, a flow velocity, flow rate, flow volume, temperature, oxygen saturation level, and/or the like of fluid delivered via and/or flowing through the intravascular reperfusion therapy device 160 (e.g., within the lumen 638). In that regard, the intravascular reperfusion therapy device 160 may include a sensor configured to obtain data internal to the intravascular reperfusion therapy device 160 (e.g., within the lumen 638). In some embodiments, the one or more sensors of the intravascular reperfusion therapy device 160 may thus be the same or different from one another. As an illustrative example, the first sensor 630 may be a flow sensor, while the second sensor 710 may be a pressure sensor or vice versa. As another example, the first sensor 630 and the second sensor 710 may each be a pressure sensor or may each be a flow sensor. Details of the configuration of the one or more sensors are provided below with respect to FIGS. 12A-12B.

Figure 6:
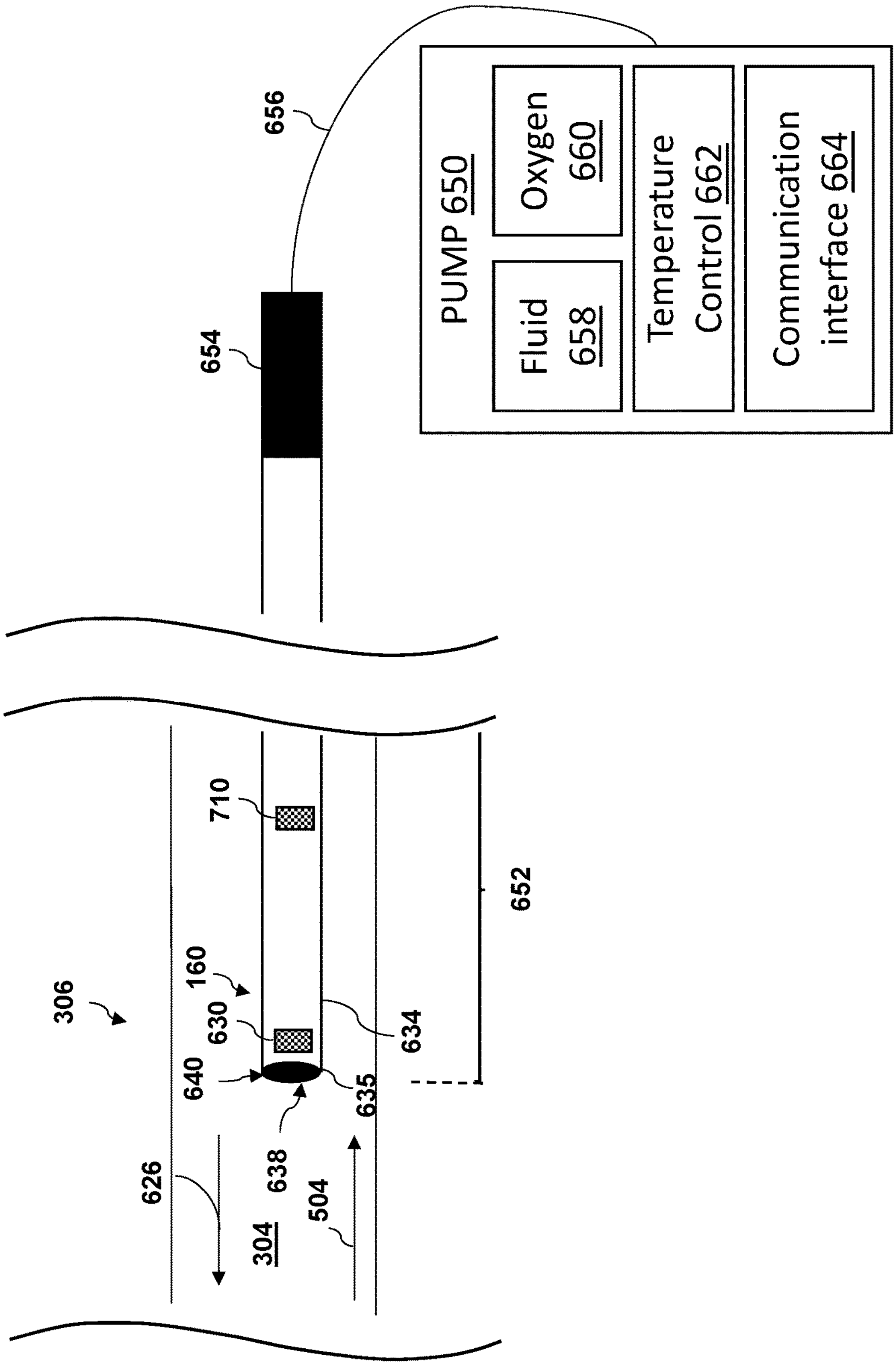
FIG. 6 is a diagrammatic side view of an intravascular reperfusion therapy device, in accordance with at least one embodiment of the present disclosure.

FIG. 6 is a diagrammatic side view of an exemplary embodiment of an intravascular reperfusion therapy device 160, which includes a pump 650 positioned external to the vasculature of a patient (e.g., positioned extravascularly) and/or positioned external to the patient. In some embodiments, the pump 650 may be configured to direct flow of a fluid (e.g., fluid 658), such as blood or saline. To that end, the pump 650 may include a pump (e.g., one or more pistons, air bladders, and/or the like), a fan, an impeller, and/or the like arranged to circulate or control the flow of the fluid 658. Moreover, to direct the flow of the fluid, the pump 650 may control the direction of the flow of the fluid, a flow rate (e.g., a flow velocity and/or a flow volume) of the fluid, and/or the like.

Further, as illustrated in FIG. 6, the distal portion 652 of the intravascular reperfusion therapy device 160 may be configured (e.g., sized and shaped) to be positioned within the vasculature of the patient, such as within a coronary vein 304 (e.g., the coronary sinus 306) of the patient. In some embodiments, the distal portion 652 of the intravascular reperfusion therapy device 160 may include one or more sensors, such as the sensor 630 and the second sensor 710. As described herein, the sensor 630 and the second sensor 710 may be may be the same (e.g., configured to sense the same parameter) or different (e.g., configured to different parameters) from one another. Moreover, in some embodiments, the sensor 630 may be configured to sense physiological data associated with a first region within a patient's vasculature, while the second sensor 710 may be configured to sense physiological data associated with a different, second region within the patient's vasculature, which may be spaced from the first region. For instance, as illustrated, the second sensor 710 may be positioned proximal of the first sensor 630 and may be configured to obtain physiological data from a location within the vasculature proximal of the first sensor 630 and/or the region sensed by the first sensor 630. As an illustrative example, the distal portion 652 may be arranged such that the first sensor 630 is positioned within and obtains physiological data from the coronary sinus 306, while the second sensor 710 is positioned within and obtains physiological data from the vena cava of the patient. Additionally or alternatively, the sensors (e.g., 630, 710) may be arranged such that the first sensor 630 obtains physiological data associated the reperfusion therapy delivered by the device 160, such as data associated with the pressure changes in the coronary vein 304 and/or other blood flow characteristics associated with the coronary vein 304 and/or the targeted area of tissue 310. The second sensor 710 may be arranged such that the second sensor 710 obtains physiological data representative of blood flow spaced from the delivery of the reperfusion therapy (e.g., spaced from the target are of tissue) and/or relatively unaffected by the reperfusion therapy. In this regard, the first sensor 630 may be arranged to obtain "local" physiological data, which can refer to data representative of the influence of the intravascular reperfusion therapy device 160 on blood flow proximate the distal end 640 of the catheter 634, and the second sensor 710 may be arranged to obtain "global" physiological data, which can refer to data representative of the overall blood flow characteristics of the patient and/or data representative of blood flow characteristics relatively unaffected by the intravascular reperfusion therapy device 160. Further, embodiments of the intravascular reperfusion therapy device 160 are not limited to the arrangement (e.g., spacing) of the sensors (e.g., 630, 710) described above. In that regard, one or more sensors may be positioned proximate to one another on the intravascular reperfusion therapy device 160.

The intravascular reperfusion therapy device 160 may include a connector 654, which may couple the distal portion 652 to the pump 650. In particular, as illustrated, the connector 654 may be coupled to the pump 650 via tubing 656 (e.g., one or more conduits and/or wiring). In that regard, the pump 650 may be coupled to the distal portion 652 and, in particular, the lumen 638 and/or the port 635 via the tubing 656. In this way, the pump 650 may deliver fluid (e.g., blood and/or saline) to the coronary vein 304 via the catheter 634, and/or the pump 650 may receive fluid relocated from the coronary vein 304 via the catheter 634. That is, for example, the intravascular reperfusion therapy device 160 may be configured to, using the pump 650, direct the flow of fluid through the lumen to or from the coronary vein 304.

Flow of fluid from the lumen 638 of the intravascular reperfusion therapy device into the coronary vein 304 may increase a volume of total fluid in the coronary vein 304 and may generate a back flow (e.g., retrograde flow) and/or back pressure in the direction (indicated by the arrow 626) opposite the direction (indicated by the arrow 504) of blood flow (e.g., naturally occurring blood flow) in the coronary vein 304. Moreover, flow of fluid into the coronary vein 304 with relatively greater volume, velocity, and/or flow rate may cause a greater degree (e.g., level) of back flow and/or back pressure within the coronary vein 304 than flow of the fluid with relatively lesser volume, velocity, and/or flow rate. Additionally or alternatively, the flow of the fluid into the coronary vein 304 with the relatively greater volume, velocity, and/or flow rate may cause a particular back flow and/or back pressure level to be achieved within the coronary vein 304 at a faster rate than the flow of the fluid with relatively lesser volume, velocity, and/or flow rate. Further, flow of fluid from the coronary vein 304 into the lumen 638 of the intravascular reperfusion therapy device into the coronary vein 304 may decrease a volume of total fluid in the coronary vein 304 and may reduce a pressure in the coronary vein 304. Flow of fluid from the coronary vein 304 with greater volume, velocity, and/or flow rate may reduce the pressure in the coronary vein 304 to a greater degree (e.g., level) and/or at a faster rate than flow of the fluid with relatively lesser volume, velocity, and/or flow rate. In this regard, the control of flow of fluid through the lumen 638 of the intravascular reperfusion therapy device 160, such as the control of the direction and/or flow rate (e.g., flow velocity and/or flow volume) of the fluid, may correspond to control of the delivery of reperfusion therapy. In particular, the degree (e.g., level) of reperfusion therapy and/or an aggressiveness of the reperfusion therapy delivered via the intravascular reperfusion therapy device 160 may be controlled (e.g., tuned) via the control of the flow of the fluid via the pump 650, for example. More specifically, in some embodiments, the processing system 110 may control reperfusion therapy via control of the pump 650 of the intravascular reperfusion therapy device 160.

In some embodiments, the pump 650 may include the fluid 658, such as blood or saline. For example, the fluid 658 may be stored within a reservoir or other container having the fluid 658 included in or coupled to the pump 650. Further, the pump 650 may include or be coupled to a supply of oxygen 660. As further illustrated, the pump 650 may include a temperature control 662 and a communication interface 664. Moreover, in some embodiments, the pump 650 and/or the intravascular reperfusion therapy device 160 may include a processor circuit 200 (e.g., a processor), such as a microprocessor, that is configured to instruct components of the pump 650 to control aspects (e.g., oxygen saturation, temperature, and/or the like) of a fluid and/or of a delivery of the fluid, as described herein. Accordingly, while techniques described herein refer to the processing system 110 receiving data and controlling aspects of the intravascular reperfusion therapy device 160, such as operation of the pump 650, embodiments are not limited thereto. In that regard, data may be received and/or obtained at the pump 650 itself, and the processor circuit 200 of the pump 650 may control the operations of the pump 650.

In some embodiments, the intravascular reperfusion therapy device 160 may be configured to deliver and/or control reperfusion therapy by controlling the supply of oxygen to an area of tissue experiencing or having previously experienced ischemia (e.g., a reduction in delivered blood/oxygen), such as the area of tissue 310. In particular, the intravascular reperfusion therapy device 160 may be configured to control delivery of an oxygenated fluid and/or a level of oxygen (e.g., a saturation level of oxygen) in a fluid delivered to a blood vessel associated with the area of tissue 310 (e.g., targeting the area of tissue 310). For instance, increasing the level of oxygen in a fluid delivered to the blood vessel and/or increasing delivery (e.g., flow volume, velocity, and/or rate) of an oxygenated fluid to the blood vessel may increase the level of oxygen supplied to the area of tissue, which may improve the health of portion(s) of the area of tissue and/or the rate at which the health of the portion(s) of the area of tissue is improved. In this way, the level of oxygen and/or the delivery of oxygenated fluid to a blood vessel associated with the area of tissue 310 may correspond to the level (e.g., degree) of reperfusion therapy delivered to the tissue and/or the rate of delivery of the reperfusion therapy for the tissue.

In some embodiments, control of the oxygen level and/or the delivery of an oxygenated fluid to a blood vessel, such as a coronary vein 304 or a coronary artery, may be facilitated by the pump 650. For instance, the pump 650 may be configured to oxygenate the fluid 658 using the supply of oxygen 660. In particular, the pump 650 may be configured to oxygenate (e.g., mix and/or dissolve oxygen into) the fluid 658 to a level similar to or exceeding the level of oxygen in the patient's blood. For instance, the pump 650 may be configured to super-oxygenate the fluid such that the level of oxygen (e.g., the saturation level of oxygen) in the fluid delivered to the patient via the intravascular reperfusion therapy device 160 exceeds the saturation level of oxygen in the patient's level and/or exceeds a baseline saturation level of oxygen in the fluid prior to oxygenation by the pump 650. Accordingly, the supply of oxygen to an area of tissue experiencing or that previously experienced ischemia (e.g., a reduction in delivered blood/oxygen) may be restored and/or may be increased at a greater rate than a rate resulting from the supply of blood to the area of tissue alone.

In some cases, cooling (e.g., reducing the temperature) of the area of tissue 310 may reduce inflammation of the area of tissue 310, such as inflammation associated with reperfusion injury of the area of tissue 310. To that end, cooling the area of tissue 310 may improve blood flow (e.g., a level and/or a distribution of blood flow) through the area of tissue 310. Accordingly, in some embodiments, the intravascular reperfusion therapy device 160 may be configured to deliver and/or control reperfusion therapy by controlling the temperature of the area of tissue 310. In particular, the intravascular reperfusion therapy device 160 may be configured to control the temperature of fluid delivered to a blood vessel (e.g., a coronary artery 302 or a coronary vein 304) associated with the area of tissue 310 to control the temperature of the area of tissue. For instance, the intravascular reperfusion therapy device 160 may be configured to deliver a fluid with a temperature lower than a temperature of the patient's blood to the blood vessel to cool the area of tissue 310. By controlling the temperature of a fluid delivered to a blood vessel associated with an area of tissue 310 and/or the delivery (e.g., flow rate, velocity, and/or volume) of a cooling fluid (e.g., a fluid with a temperature suitable to reduce a temperature of the area of tissue 310), the intravascular reperfusion therapy device 160 may thus control the delivery of reperfusion therapy to the area of tissue 310.

In some embodiments, the pump 650 may be arranged to control the delivery (e.g., flow rate, velocity, and/or volume) of a cooling fluid to a blood vessel and/or an area of tissue using different pump rates and/or pump settings (e.g., pump volume). In some embodiments, the pump 650 may produce the cooling fluid before and/or in conjunction with delivery of the cooling fluid. As illustrated, for example, the pump 650 may include a temperature control unit 662, which may be configured to adjust (e.g., reduce) a temperature of the fluid 658 or another fluid introduced to the pump 650 to produce a fluid (e.g., a cooling fluid) with a sufficiently cool temperature, such as a temperature below a patient's blood or core temperature. The temperature control unit 662 may include a heat sink, a refrigerator, coolant (e.g., coolant circulating in one or more conduits), and/or the like, for example. In that regard, the temperature control unit 662 may be configured to reduce a temperature (e.g., draw thermal energy from) of a fluid. The temperature control unit 662 may additionally or alternatively include one or more components, such as a heat pump, configured to increase the temperature (e.g., supply thermal energy to) a fluid. For instance, the temperature control unit 662 may be equipped to increase a temperature of a fluid such that the fluid is a suitable temperature for introduction to a vasculature of a patient, such as a temperature that minimizes a patient's risk of core temperature change and/or hypothermia. In that regard, the temperature control unit 662 may further include one or more sensors (e.g., thermometers) configured to determine a temperature of the fluid in the pump 650 and/or a difference between the actual temperature of the fluid and a desired temperature of the fluid corresponding to a desired reperfusion therapy level. Moreover, in some embodiments, a cooling fluid with a sufficient temperature for a particular level (e.g., degree) of reperfusion therapy may be introduced into or included within the pump 650. That is, for example, a fluid under the control of the pump 650 may match a desired temperature for a reperfusion therapy. Accordingly, the pump 650 may refrain from adjusting the temperature of such a fluid. To that end, the temperature control unit 662 may adjust the temperature of the fluid by operating based on a feedback loop associated with a difference between an actual and a desired fluid temperature. Further, the pump 650 may output a fluid with temperature controlled by the temperature control unit 662 (e.g., a cooling fluid) to the catheter 634 (e.g., via the tubing 656) at a certain rate, resulting in a corresponding level of reperfusion therapy associated with the temperature of the cooling fluid and the delivery of the cooling fluid. To that end, the level of reperfusion therapy may be adjusted via control of the temperature and/or delivery of a cooling fluid provided via (e.g., output by) the pump 650.

The communication interface 664 may facilitate communication between components of the pump 650 and the processing system 110. To that end, the communication interface 664 may be communicatively coupled to a communication module 214 of the processing system 110. Moreover, the communication interface 664 can include any electronic circuitry and/or logic circuitry to facilitate communication of data between various components of the pump 650 with one another and/or with the processing system 110. For instance, the communication interface 664 may include one or more antennas, electrical wires, transceivers, and/or the like. In some embodiments, the communication interface 664 can be an input/output (I/O) device interface, which may facilitate communicative coupling between the processing system 110 and the pump 650 and/or between components of the pump 650. Moreover, the communication interface 664 may facilitate wireless and/or wired communication between various elements of the pump 650, and the communication interface 664 may facilitate wireless communication between the pump 650 and the processing system 110. The communication interface 664 may facilitate such communication using any suitable communication technology, such as a cable interface such as a USB, micro USB, Lightning, or FireWire interface, Bluetooth, Wi-Fi, RF data transmission, ZigBee, Li-Fi, or cellular data connections such as 2G/GSM, 3G/UMTS, 4G/LTE/WiMax, or 5G.

In some embodiments, the intravascular reperfusion therapy device 160 and/or the processing system 110 may be configured to oscillate operation of the pump 650 to adjust delivery of fluid and the resulting reperfusion therapy delivered to a target area (e.g., the area of tissue 310). For instance, to intermittently (e.g., periodically or aperiodically) generate back pressure (e.g., in the direction indicated by the arrow 626) and/or alter a pressure within the coronary vein 304, the processing system 110 may control the intravascular reperfusion therapy device 160 (e.g., using the pump 650) to switch between delivery of fluid with first flow characteristics to delivery of flow with different, second flow characteristics. The first flow characteristics may correspond to a first combination of flow rate, flow velocity, and/or flow volume, for example, and the second flow characteristics may correspond to a different, second combination of flow rate, flow velocity, and/or flow volume. As an illustrative example, the processing system 110 may control the intravascular reperfusion therapy device 160 to actively pump fluid (e.g., with the pump 650) into the coronary vein 304 for a certain duration and may then control the intravascular reperfusion therapy device 160 to not pump fluid into the coronary vein 304 (e.g., to pause operation of the pump 650 and/or to control the pump 650 to direct fluid from the coronary vein 304 into the port 635). Actively pumping the fluid into the coronary vein 304 may increase the back pressure (e.g., in the direction 626) within the coronary vein, not pumping fluid into the coronary vein 304 may allow pressure within the coronary vein 304, including the back pressure, to reduce, and the combination of the two may affect reperfusion therapy at a target tissue. Further, in the above example, the processing system 110 may further switch between the two different controls of the intravascular reperfusion therapy device 160 to oscillate operation of the pump 650. The processing system 110 may additionally or alternatively control the intravascular reperfusion therapy device 160 such that the pump 650 continually delivers fluid to the coronary vein 304 over a duration and varies and/or oscillates characteristics of the fluid delivery over the duration. For instance, the pump 650 may continuously deliver fluid in a first direction (e.g., into the coronary vein 304), and, during this delivery, the pump 650 may change the instantaneous volume, velocity, and/or rate of fluid delivered to a target (e.g., a blood vessel) in the first direction.

In some embodiments, the processing system 110 may control (e.g., oscillate) operation of the intravascular reperfusion therapy device 160 and a resulting flow of fluid directed by the device 160 according to a set pattern (e.g., combination of frequency, duty cycle, duration, and/or the like). For instance, the processing system 110 may include instructions (e.g., instructions 216) to deliver a predetermined reperfusion therapy via a set (e.g., predetermined) control (e.g., oscillation) of the intravascular reperfusion therapy device 160 and/or the pump 650. Additionally or alternatively, the processing system 110 may be configured to control the delivery of the reperfusion therapy (e.g., via control of the pump 650) based on a user input, which may be received via the input device 130, for example. Moreover, in some embodiments, the processing system 110 may be configured to monitor a progression of the reperfusion therapy and adaptively control the delivery of the reperfusion therapy based on the progression of the reperfusion therapy. For instance, as described with respect to FIG. 8, the processing system 110 may control the delivery of the reperfusion therapy based on information (e.g., physiological data) received from the one or more sensors (e.g., the first sensor 630 and/or the second sensor 710) of the intravascular reperfusion therapy device 160. That is, for example, the processing system 110 may control delivery of the therapy via a feedback loop with the intravascular reperfusion therapy device 160.

Figure 7:
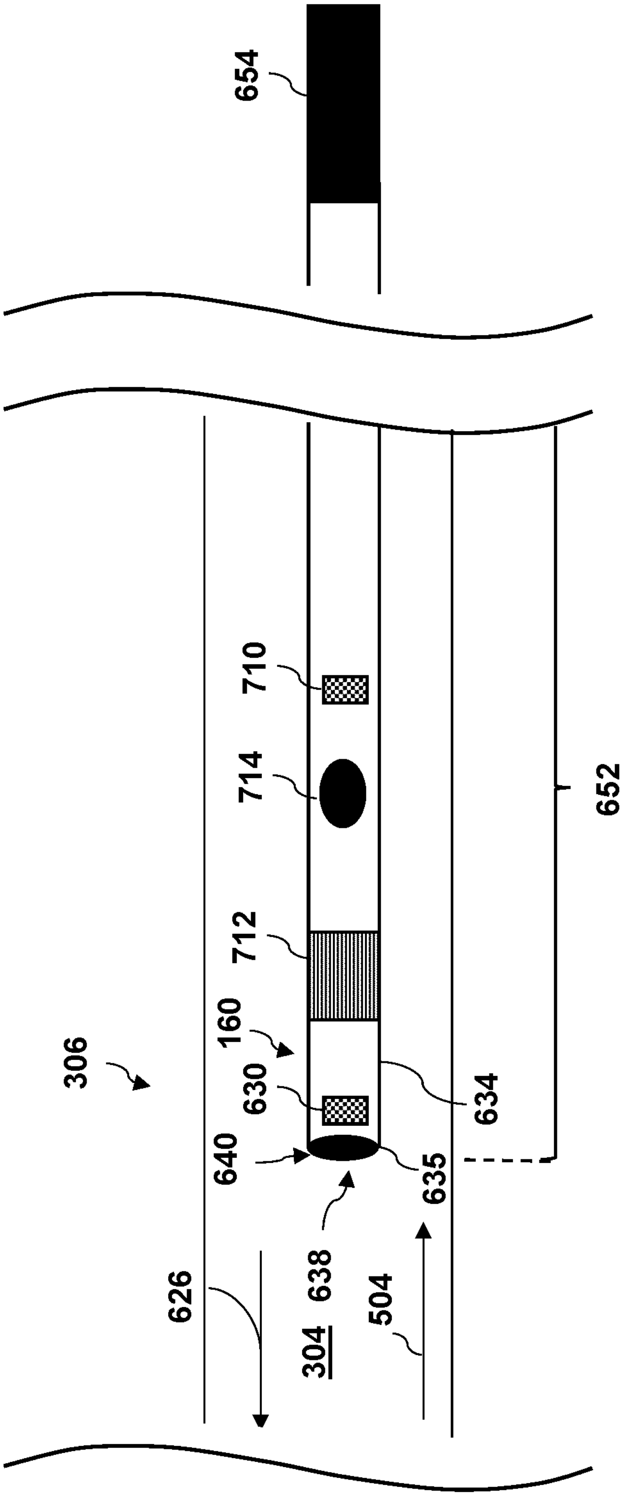
FIG. 7 is a diagrammatic side view of an intravascular reperfusion therapy device, in accordance with at least one embodiment of the present disclosure.

FIG. 7 is a diagrammatic side view of an exemplary embodiment of an intravascular reperfusion therapy device 160, which includes an intravascular pump 712 and a second port 714. The intravascular pump 712 may be configured (e.g., sized and shaped) to be positioned within a patient's vasculature, such as within a coronary vein 304. The intravascular pump 712 may be arranged to direct flow of fluid within the lumen 638 by, for example, controlling a direction, a flow volume, a flow velocity, and/or a flow rate of the fluid. In some embodiments, the intravascular pump 712 may include a fan, one or more pistons, an impeller, and/or the like that may direct the flow of the fluid. Further, in some embodiments, the intravascular pump 712 may include or be coupled to one or more components described with respect to the pump 650. For instance, the intravascular pump 712 may include a temperature control unit 662, one or more sensors associated with the temperature control unit 662 (e.g., thermometers), and/or a communication interface 664. In some embodiments, the intravascular pump 712 may additionally or alternatively be in fluid communication with a supply of a fluid (e.g., fluid 658), such as blood or saline, and/or a supply of oxygen (e.g., oxygen 660). For instance, the supply of fluid and/or the supply of oxygen may be positioned external to the patient and may be coupled to the intravascular pump 712 via tubing (e.g., one or more conduits) connected to the connector 654. Moreover, in some embodiments, temperature control (e.g., via the temperature control unit 662) may further be performed on the supply of fluid external to the patient. In embodiments where the intravascular reperfusion therapy device 160 includes the intravascular pump 712 in fluid communication with one or more external components (e.g., fluid, oxygen, temperature control, and/or the like), the intravascular reperfusion therapy device 160 may include one of the port 635 or the second port 714. Accordingly, while the intravascular reperfusion therapy device 160 is illustrated as having the intravascular pump 712 and each of the port 635 and the second port 714, embodiments are not limited thereto.

FIG. 7 further illustrates that, in some embodiments, the intravascular reperfusion therapy device may include a second port 714. As illustrated, the second port 714 may be formed in a sidewall of the catheter 634, and the second port 714 may be in fluid communication with the lumen 638. In some embodiments, the intravascular pump 712 may be configured to direct flow of fluid such that the intravascular reperfusion therapy device 160 intakes fluid from the port 635 and outputs the fluid via the second port 714. As illustrated, the second port 714 may be spaced from and proximal to the first port 635. Accordingly, directing flow from the port 635 to the second port 714 may reduce pressure proximate the distal end 640 in the coronary vein 304. As an illustrative example, the port 635 may be positioned within the coronary sinus 306, while the second port 714 may be positioned within the vena cava of a patient. Continuing with this example pumping, using the intravascular pump 712, fluid out the second port 714 may reduce pressure in the coronary sinus 306 by increasing fluid flow to the vena cava. Further, in some embodiments, the intravascular pump 712 may be configured to direct flow of fluid such that the intravascular reperfusion therapy device 160 intakes fluid from the second port 714 and outputs the fluid via the port 635. Directing flow from the second port 714 to the port 635 may generate a back pressure (e.g., in the direction indicated by arrow 626) within the coronary vein, such as proximate the distal end 640 within the coronary vein 304.

In some embodiments, the sensor 630 may be configured to obtain physiological data corresponding to blood flow associated with (e.g., proximate) the port 635. Further, the sensor 710 may be configured to obtain physiological data corresponding to blood flow associated with (e.g., proximate) the second port 714. Moreover, flow of fluid into or out of each of the ports (e.g., 635, 714) may be controlled based on the physiological data obtained by the sensor 630 and/or the physiological data obtained by the second sensor 710, as described in greater detail below.

While the pump 712 is illustrated as being positioned between the port 635 and the second port 714 (e.g., where the port 635 is distal of the pump 712 and the second port 714 is positioned proximal of the pump 712), embodiments are not limited thereto. In that regard, in some embodiments, the port 635 and the second port 714 are positioned distal of the pump 712. Further, in some embodiments, the port 635 and the second port 714 are positioned proximal of the pump 712. For instance, the pump 712 may be positioned proximate the distal end 640, which may or may not be sealed (e.g., including a third port, for example), and the port 635 and the second port 714 may be formed in the sidewall of the catheter 634 proximal of the pump 712. Moreover, it may be appreciated that the intravascular reperfusion therapy device 160 may include any suitable number (e.g., one, two, three, five, ten, and/or the like) of ports.

While the present disclosure describes embodiments of the intravascular reperfusion therapy device including a controllable pump and a lumen for fluid (e.g., saline, oxygen), it is understood that the intravascular reperfusion therapy device can include any suitable structure that selectively restricts blood flow and/or generates back pressure. For example, the structure can be the pump and lumen. The structure can be an obstruction in some embodiments. For example, the obstruction can be an expandable structure (e.g., expandable balloon, open/close valve or valve stent, expandable basket, expandable multi-arm structure with or without material in between the arms) that can be controlled to be in one state (closed valve, expanded balloon, or expanded basket/arms restricting blood flow) and another state (open valve, contracted balloon, or contracted basket/arms allowing blood flow).

Figure 8:
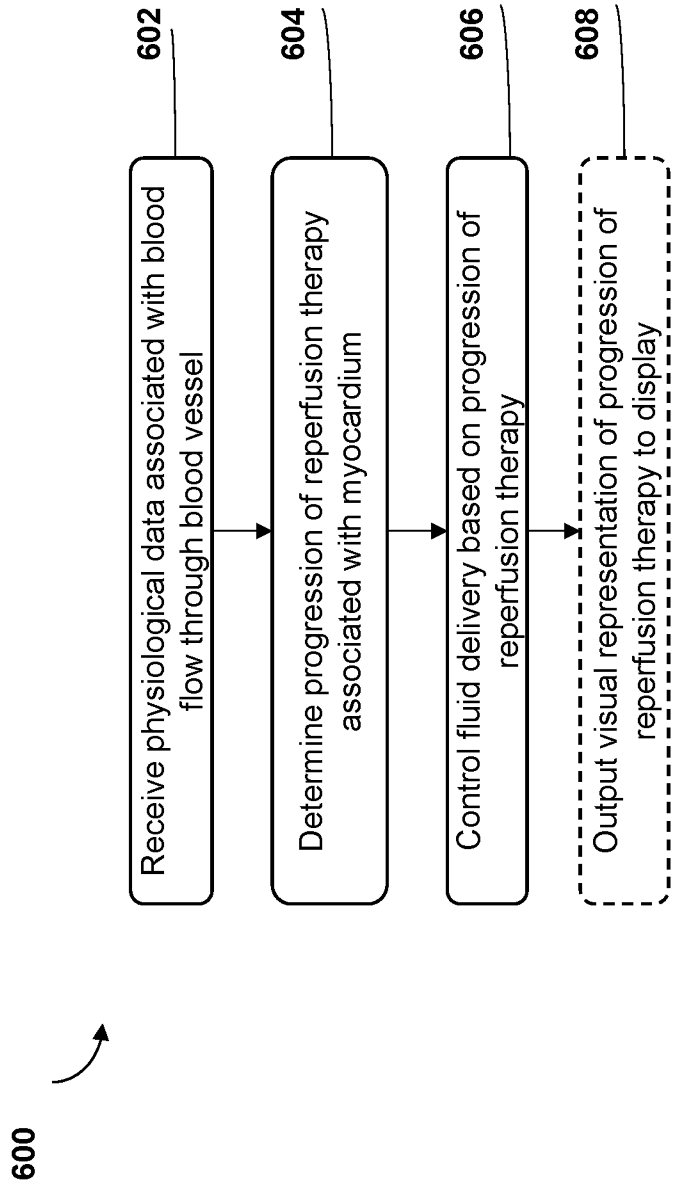
FIG. 8 is a flow diagram of a method for evaluating a progression of a reperfusion therapy, in accordance with at least one embodiment of the present disclosure.

FIG. 8 is a flow diagram of a method 800 of evaluating (e.g., assessing) and controlling (e.g., modifying) a progress of reperfusion of a tissue, according to aspects of the present disclosure. In some embodiments, the method 800 may be used to control a reperfusion therapy, which may be delivered via a device, such as the intravascular reperfusion therapy device 160 of FIG. 1. In particular, the method 800 may be used to control an intravascular reperfusion therapy device positioned within a blood vessel associated with an area of tissue that reperfusion therapy is targeting, such as the device 160 illustrated in FIG. 5. As an illustrative example, the blood vessel may be a coronary blood vessel, such as a coronary vein, and the area of tissue may be a myocardium (e.g., muscular tissue of the heart). The method 800 may additionally or alternatively be used to control a reperfusion therapy targeting microvascular disease (e.g., affecting capillary beds, for example) in any portion of a patient's anatomy (e.g., within or separate from the heart) and/or nonobstructive coronary artery disease. Further, in some cases, the area of tissue may be an area of tissue that receives an increase in blood flow, which may result from administration of a therapy, such as a PCI therapy.

As illustrated, the method 800 includes a number of enumerated steps, but embodiments of the method 800 may include additional steps before, after, or in between the enumerated steps. In some embodiments, one or more of the enumerated steps may be omitted, performed in a different order, or performed concurrently. The steps of the method 800 can be carried out by any suitable component within the system 100 and all steps need not be carried out by the same component. In some embodiments, one or more steps of the method 800 can be performed by, or at the direction of, a processor circuit of the system 100, including, the processing system 110 (e.g., the processor 210 (FIG. 2)) or any other component. For the purposes of example, method 800 is described with respect to features illustrated in FIGS. 1, 2, and 4-7. The description with respect to these features is intended to be illustrative and not limiting.

At step 802, the method 800 involves receiving physiological data associated with blood flow through a blood vessel. In particular, the physiological data may be associated with blood flow through a blood vessel that is associated with an area of tissue targeted for reperfusion therapy. As an illustrative example, the blood vessel may be a coronary blood vessel, such as a coronary vein (e.g., the coronary sinus 306 or another suitable vein), and the area of tissue may be a myocardium (e.g., muscular tissue of the heart) associated with the coronary vein. For instance, deoxygenated blood may flow from the myocardium to the associated coronary vein, as illustrated by the relationship of the area of tissue 310 with the coronary vein 304 and the coronary sinus 306 shown in FIGS. 4-5. For the purposes of example, the method 800 is described herein with respect to a myocardium (e.g., the area of tissue 310) and a coronary vein, such as the coronary sinus 306. However, embodiments are not limited thereto.

The processing system 110 may receive the physiological data from the one or more sensors (e.g., the first sensor 630 and/or the second sensor 710) of the intravascular reperfusion therapy device 160. Moreover, the one or more sensors may obtain the physiological data from within the blood vessel (e.g., intravascularly), as illustrated by the arrangement of the intravascular reperfusion therapy device 160 shown in FIG. 5. To that end, the processing system 110 may receive the physiological data while the one or more sensors are positioned within the blood vessel.

In some embodiments, the physiological data may include flow data, such as a flow rate or flow velocity of blood through the blood vessel. Additionally or alternatively, the physiological data may include pressure data, such as measurements of blood pressure within the blood vessel. Further, the physiological data may include data associated with the anatomy of the blood vessel, such as a diameter of the blood vessel, a distance between a component of the intravascular reperfusion therapy device and a wall of the blood vessel, and/or the like. In some embodiments, the physiological data may additionally or alternatively include intravascular imaging data, such as IVUS imaging data, OCT imaging data, and/or the like, obtained by the intravascular reperfusion therapy device 160. Moreover, the physiological data may include data from the sensor 630 and/or the second sensor 710. The data from the sensor 630 may correspond to the same parameters as the data from the second sensor 710 or different parameters. For instance, each of the data from the sensor 630 and the data from the second sensor 710 may include flow data, or the data from the sensor 630 may correspond to pressure data, while the data from the second sensor 710 may correspond to flow data.

In some embodiments, the processing system 110 may further receive external imaging data associated with the blood vessel and/or the area of tissue associated with the blood vessel. For instance, the processing system 110 may receive imaging data obtained by the external imaging device 140, such as one or more include x-ray images, CT images, MRI images, SPECT images, external ultrasound images, and/or the like. The external imaging data may include contrast (e.g., may be obtained using contrast), which may be delivered by the contrast infusion pump 170, for example, such that blood flow and/or anatomical features may be visibly identified. In that regard, physiological data associated with the blood flow through the blood vessel may further be received and/or determined via external imaging data.

Further, in some embodiments, the processing system 110 may receive data associated with a pump (e.g., pump 650 and/or intravascular pump 712) of the intravascular reperfusion therapy device 160 and/or the fluid under the control of the intravascular reperfusion therapy device 160 (e.g., via the pump). For instance, the processing system 110 may receive data indicating a temperature, oxygen saturation level, and/or the like of the fluid under the control of the intravascular reperfusion therapy device 160, such as fluid being delivered to or directed (e.g., pumped) away from the coronary vein 304. The processing system 110 may additionally or alternatively receive data representative of the flow rate, flow volume, flow velocity, flow direction, and/or the like. For instance, the pump may provide such data to the processing system via the communication interface 664 in some embodiments. Additionally or alternatively, the pump may communicate operating characteristics, such as an output power of the pump, and the processing system 110 may determine data representative of flow of the fluid based on these characteristics.

At step 804, the method 800 may involve determining a progression of a reperfusion therapy. That is, for example, a progression of a reperfusion therapy targeting an area of tissue (e.g., myocardium) associated with the blood vessel corresponding to the physiological data may be determined. In that regard, the reperfusion therapy may be a therapy delivered by the intravascular reperfusion therapy device 160 to an area of tissue 310 (e.g., myocardium). Moreover, the reperfusion therapy may regulate blood flow to the targeted tissue in some manner. In particular and as illustrated in FIG. 5, the intravascular reperfusion therapy device 160 may generate a back pressure and/or back flow in a direction (e.g., indicated by arrow 626) opposite the flow of blood (e.g., indicated by arrow 504) within the blood vessel. The back pressure and/or back flow may change a pressure and/or resistance/impedance at the area of tissue 310, which may affect the distribution of blood flowing into (e.g., indicated by the arrow 502) the microvasculature (e.g., capillary bed) of the area of tissue 310. In that regard, the reperfusion therapy may be delivered such that blood suitably perfuses throughout the area of tissue 310, including to portions of the tissue 310 that are inflamed or damaged.

In some embodiments, determining a progression of the reperfusion therapy (e.g., at step 804) may involve determining a characteristic of blood flow through the blood vessel (e.g., a coronary vein 304) and/or through the area of tissue 310 (e.g., myocardium). In that regard, the processing system 110 may determine the progression of the reperfusion therapy delivered via the intravascular reperfusion therapy device 160 based on physiological data, such as physiological data received from the intravascular reperfusion therapy device 160 and/or external imaging data received from the external imaging device 140. For instance, based on the physiological data (e.g., pressure data, flow data, external imaging data, and/or the like) and/or data corresponding to the pump (e.g., 650, 712) of the device 160, the processing system 110 may determine a flow velocity, a flow rate, and/or a pressure of blood within the blood vessel. The processing system 110 may additionally or alternatively determine a volume of blood and/or a resistance/impedance to blood flow within the blood vessel using the physiological data. For instance, the processing system 110 may determine the resistance and/or the impedance based on flow data and pressure data, in some embodiments.

The processing system 110 may relate a determined value (e.g., level) and/or change thereof of flow velocity, flow rate, pressure, volume, resistance/impedance, and/or the like to a progression of the reperfusion therapy. In general, the processing system 110 may associate a progression of a reperfusion therapy that produces values of such parameters or changes in these values indicating greater and/or increasing blood flow through the blood vessel as relatively effective (e.g., as having a positive and/or intended effect). Further, the processing system 110 may associate a progression of a reperfusion therapy that produces values of such parameters or changes in these values indicating lower, unchanging, and/or decreasing blood flow through the blood vessel as relatively ineffective (e.g., as having a negative and/or unintended effect).

More specifically, in some embodiments, the processing system 110 may compare the determined values of such parameters (e.g., parameters associated with blood flow) to one or more thresholds or other values. As an illustrative example, a first range of values may correspond to healthy blood flow conditions, while a second range of values may correspond to unhealthy blood flow conditions. To that end, responsive to determining that a value of a parameter falls within the first range (e.g., satisfies a threshold), the processing system 110 may determine that the reperfusion therapy is complete, and responsive to determining that a value of a parameter falls within the second range (e.g., fails to satisfy a threshold), the processing system 110 may determine that additional reperfusion therapy may be delivered to the target area of tissue. In some embodiments, the first range of values and/or the second range of values may be determined on historical data associated with other patients, historical data associated with the patient, data associated with a healthy blood vessel (e.g., a vessel relatively unaffected by or not associated with the blockage 308) of the patient, and/or the like.

Additionally or alternatively, the processing system 110 may determine the change in value of such parameters over the delivery of the reperfusion therapy (e.g., over time) and may relate this change to the progression of the reperfusion therapy. In some embodiments, for example, the processing system 110 may compare a current value of a parameter with a set of one or more previous values of the parameter and/or determine a derivative of the parameter with respect to time. For instance, the processing system 110 may determine a derivative of the physiological data and/or of a parameter determined based on the physiological data with respect to time. To that end, the processing system 110 may determine whether a value of the physiological data and/or the parameter is increasing, decreasing, or relatively unchanging. Moreover, the processing system 110 may determine a rate of change of the value of the physiological data and/or the parameter. In this way, the processing system 110 may determine whether the reperfusion therapy is improving blood flow to the area of tissue 310 and/or the rate at which the reperfusion therapy is impacting the blood flow to the area of tissue 310. That is, for example, the processing system 110 may determine an efficacy and/or an efficiency of the reperfusion therapy.

In some embodiments, the processing system 110 may compare the change in the value of the parameter and/or the derivative of the parameter to one or more thresholds to determine a progression of the reperfusion therapy. For instance, a first range of values may correspond to the reperfusion therapy demonstrating improvement for (e.g., a positive effect on) the area of tissue, a second range may correspond to the reperfusion therapy demonstrating worsening blood flow conditions at the area of tissue, and a third range may correspond to the reperfusion therapy demonstrating having no effect or a relatively small effect on the area of tissue. Such thresholds may additionally or alternatively be used to quantify a degree of an effect the reperfusion therapy has on the tissue area. Moreover, the processing system 110 may use the physiological data and/or derivatives thereof to determine when the reperfusion therapy is complete by determining whether the value of one or more parameters has reached a healthy threshold or has plateaued at a maximum value.

Further, the progression of the reperfusion therapy may additionally or alternatively be determined based on external imaging data obtained by the external imaging device 140. For instance, in some embodiments, the processing system 110 may determine changes in blood flow (e.g., changes in flow velocity, flow rate, and/or the like) through a vessel over time (e.g., before, during, and/or after delivery of reperfusion therapy) based on external imaging data (e.g., from the external imaging device 140). For instance, using imaging processing techniques, the processing system 110 may identify a change in a blood flow through a blood vessel based on a change in an intensity, contrast, brightness, color, and/or the like of an area (e.g., an image element and/or a pixel) of external image data obtained with contrast. An example of image processing includes conducting a pixel level analysis to evaluate whether there is a change in the color of the pixel between different images in external image data captured over different time points. Continuing with this example, for external imaging data obtained with a contrast that decreases exposure of blood (e.g., on an x-ray detector in conjunction with the x-ray source), a change in pixel color from a lighter color (e.g., gray or white) to a darker color (e.g., black) within different external images may indicate an increase in blood flow (e.g., blood perfusion) through an area (e.g., blood vessel and/or tissue) associated with the pixel, which may correspond to a progression of the reperfusion therapy providing improvement to a patient's health. A change in pixel color from a darker color to a lighter color, on the other hand, may indicate a decrease in blood flow through the area, which may correspond to a progression of the reperfusion therapy providing a negative effect on a patient's health. Moreover, as similarly described with the values of physiological data and/or parameters associated with the data, changes in blood flow and/or external imaging data characteristics (e.g., intensity, contrast, brightness, and/or the like) identified based on external imaging data may be compared to one or more thresholds and/or may be further evaluated to determine the progression of the reperfusion therapy and/or a rate of the progression of the reperfusion therapy.

At step 806, the method 800 may involve controlling the reperfusion therapy based on the determined progression of the reperfusion therapy (e.g., based on the physiological data associated with the blood flow through the blood vessel). In some embodiments, for example, the processing system 110 may control and/or instruct the intravascular reperfusion therapy device 160 based on the progression of the reperfusion therapy. For instance, in the case of reperfusion therapy being delivered venously, the intravascular reperfusion therapy device 160 may be configured to generate a back pressure (in the direction indicated by the arrow 626) in the coronary vein 304 via delivery of a fluid (e.g., blood and/or saline) having retrograde flow with respect to the flow of blood (indicated by the arrow 504) in the coronary vein 304. Moreover, the intravascular reperfusion therapy device 160 may oscillate (e.g., intermittently change) the pressure in the coronary vein 304 to different levels. For instance, the intravascular reperfusion therapy device 160 may control the pressure between a first pressure, which may result from the delivery of the fluid having the retrograde flow, and a lower, second pressure, which may result from the intravascular reperfusion therapy device 160 pausing, halting, or reducing (e.g., changing flow characteristics of) the delivery of the fluid. To control or adjust the reperfusion therapy, the processing system 110 may thus modify the delivery of the fluid from the intravascular reperfusion therapy device 160 to the coronary vein. In particular, the processing system 110 may control the intravascular reperfusion therapy device 160 to control (e.g., via the pump) the delivery of the fluid. For instance, the frequency, duty cycle, duration, and/or the like of the oscillation of the pressure within the coronary vein 304 may be controlled via oscillation of pump (e.g., 650 and/or 712) operating characteristics, which may correspond to the volume, direction, velocity, and/or rate at which the pump directs the flow of fluid through the intravascular reperfusion therapy device 160. To that end, increasing, using the pump, the flow velocity, flow volume, and/or flow rate of fluid delivered to the coronary vein (e.g., pumped in a first direction) may increase back pressure within the coronary vein, while decreasing, using the pump, the flow velocity, flow volume, and/or flow rate of fluid delivered to the coronary vein 304 may decrease the back pressure within the coronary vein 304. Moreover, increasing, using the pump, the flow velocity, flow volume, and/or flow rate of fluid received from the coronary vein 304 (e.g., pumped in an opposite, second direction) into the intravascular reperfusion therapy device (e.g., via the port 635) may decrease the pressure within the coronary vein 304.

To control the reperfusion therapy, the processing system 110 may additionally or alternatively control the temperature and/or oxygen saturation level of fluid delivered to the coronary vein 304 (e.g., targeting the area of tissue 310). For instance, as described above, the processing system 110 may, via control of the intravascular reperfusion therapy device 160 and/or its pump, increase the oxygen saturation level of the fluid and/or decrease the temperature of the fluid delivered to the coronary vein 304 to provide a greater degree of reperfusion therapy.

In some embodiments, based on the determined progression of the reperfusion therapy indicating that the progression is relatively poor, not effective, and/or that blood flow is not improving in the blood vessel, the processing system 110 may control the intravascular reperfusion therapy device 160 to increase back pressure resulting on the venous side of the tissue (e.g., via fluid controlled by the pump 650 and/or 714). In that regard, the processing system 110 may instruct the intravascular reperfusion therapy device 160 such that a blood flow (e.g., blood perfusion) through the area of tissue 310 is increased. As an illustrative example, increasing a flow rate, a flow velocity, and/or a flow volume of fluid delivered by the intravascular reperfusion therapy device 160 to the coronary vein 304 may increase the back pressure and/or back flow, as well as an aggressiveness of the reperfusion therapy. The processing system 110 may additionally or alternatively increase the oxygenation (e.g., using the oxygen supply 660) of and/or decrease the temperature (e.g., using the temperature control unit 662) of the fluid delivered to the coronary vein 304 responsive to determining that the reperfusion therapy is relatively poor, ineffective, and/or that blood flow through the vessel is not improving.

Further, based on the determined progression of the reperfusion therapy indicating that the progression is relatively good, effective, and/or that the blood flow is improving in the blood vessel, the processing system 110 may instruct the intravascular reperfusion therapy device 160 to maintain a current therapy (e.g., delivery of fluid, temperature of the fluid, and/or oxygenation of the fluid) and/or to gradually terminate (e.g., ease off) delivery of the therapy. Continuing with the above example, decreasing the flow volume, flow velocity, and/or flow rate of the fluid delivered to the coronary vein 304 and/or pausing delivery of the fluid to the coronary vein 304 may decrease the back pressure and/or back flow, as well as an aggressiveness of the reperfusion therapy. In general, the processing system 110 may adjust one or more characteristics of the intravascular reperfusion therapy device 160 operation (e.g., operation characteristics of the pump 650 and/or 712) based on a feedback loop with the intravascular reperfusion therapy device 160 and the determined progression of the reperfusion therapy. In that regard, it may be appreciated that steps of the method 800 may be repeated, such that the processing system 110 may continually determine a current progression of the reperfusion therapy (e.g., based on updated physiological data) and adaptively adjust the operation of the intravascular reperfusion therapy device 160 and/or the operation of the pump (e.g., 650 and/or 714).

Figure 9:
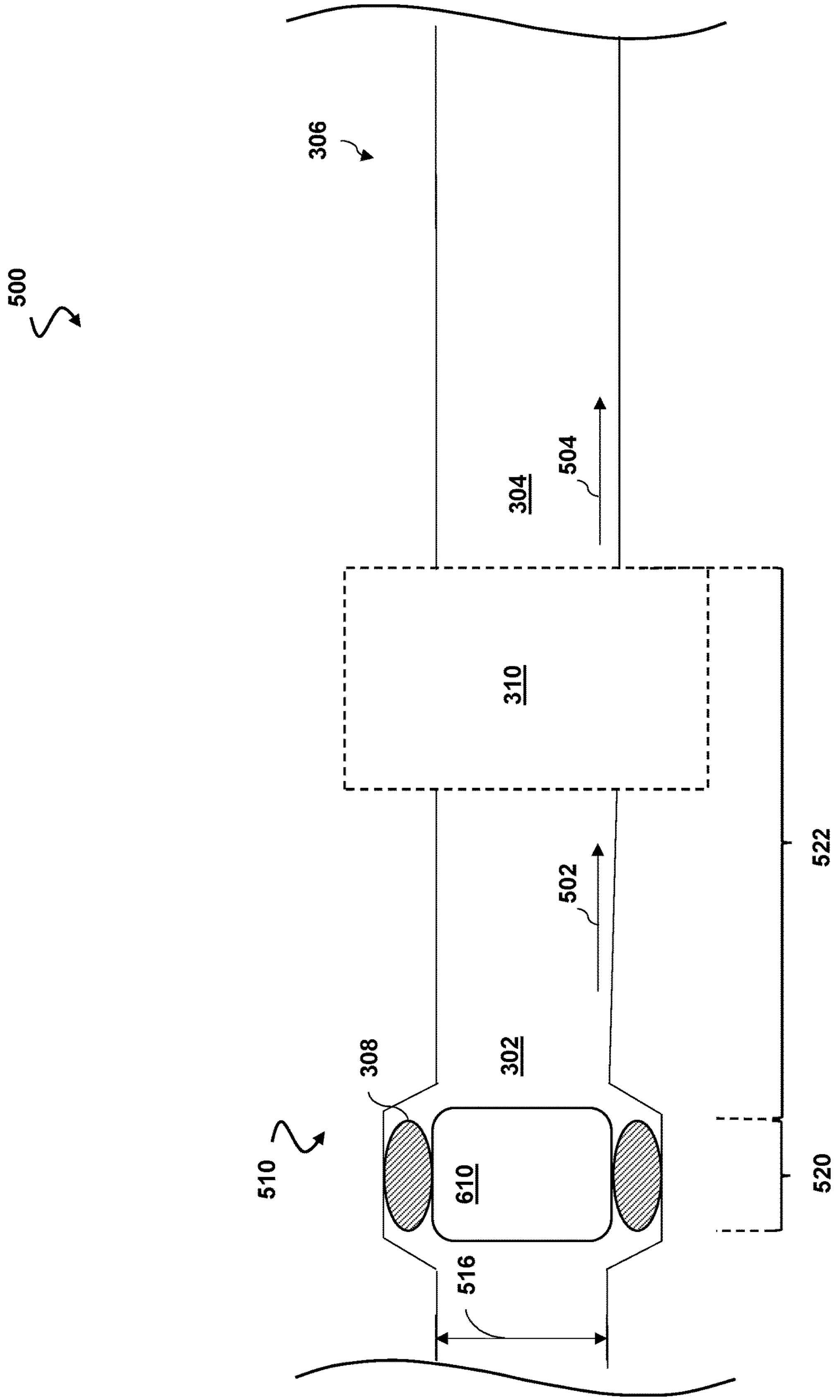
FIG. 9 is a schematic diagram of a portion of a heart, in accordance with at least one embodiment of the present disclosure.

In some embodiments, responsive to determining that the blood flow through the first area has reached a healthy level (e.g., satisfies a threshold), has reached a level substantially similar to blood flow through the second area, has plateaued at a maximum value, the processing system 110 may determine that the progression of the reperfusion therapy has reached completion. In such cases, the processing system 110 may control the intravascular reperfusion therapy device 160 to terminate delivery of the reperfusion therapy. For instance, the processing system 110 may, via control of the pump 650 and/or 714, halt delivery of fluid to the coronary vein 304 from the intravascular reperfusion therapy device 160 to terminate the delivery of the reperfusion therapy (e.g., responsive to determining the therapy has reached completion). FIG. 9 provides an illustrative example of the portion 500 of the heart after reperfusion therapy is complete, as illustrated by the absence of the intravascular reperfusion therapy device 160. In that regard, FIG. 9 may correspond to a detailed view of a portion of the heart 300 illustrated in FIG. 3C. As described above, when reperfusion therapy is complete, the blood flow in the first area of tissue 310 may be greater than a blood flow amount following a PCI therapy and/or may be substantially similar to the blood flow in healthy tissue, such as tissue unaffected and/or not associated with a vessel including a blockage.

With reference again to FIG. 8, at step 808, the method 800 may optionally involve (as indicated by the dashed lines) outputting a visual representation of the progression of the reperfusion therapy to a display. For instance, the processing system 110 may output a screen display (e.g., a graphical user interface (GUI)) including a representation of the progression of the reperfusion therapy to the display device 120. An example of a screen display including a representation of the progression of the reperfusion therapy is illustrated and described with respect to FIG. 10.

Figure 10:
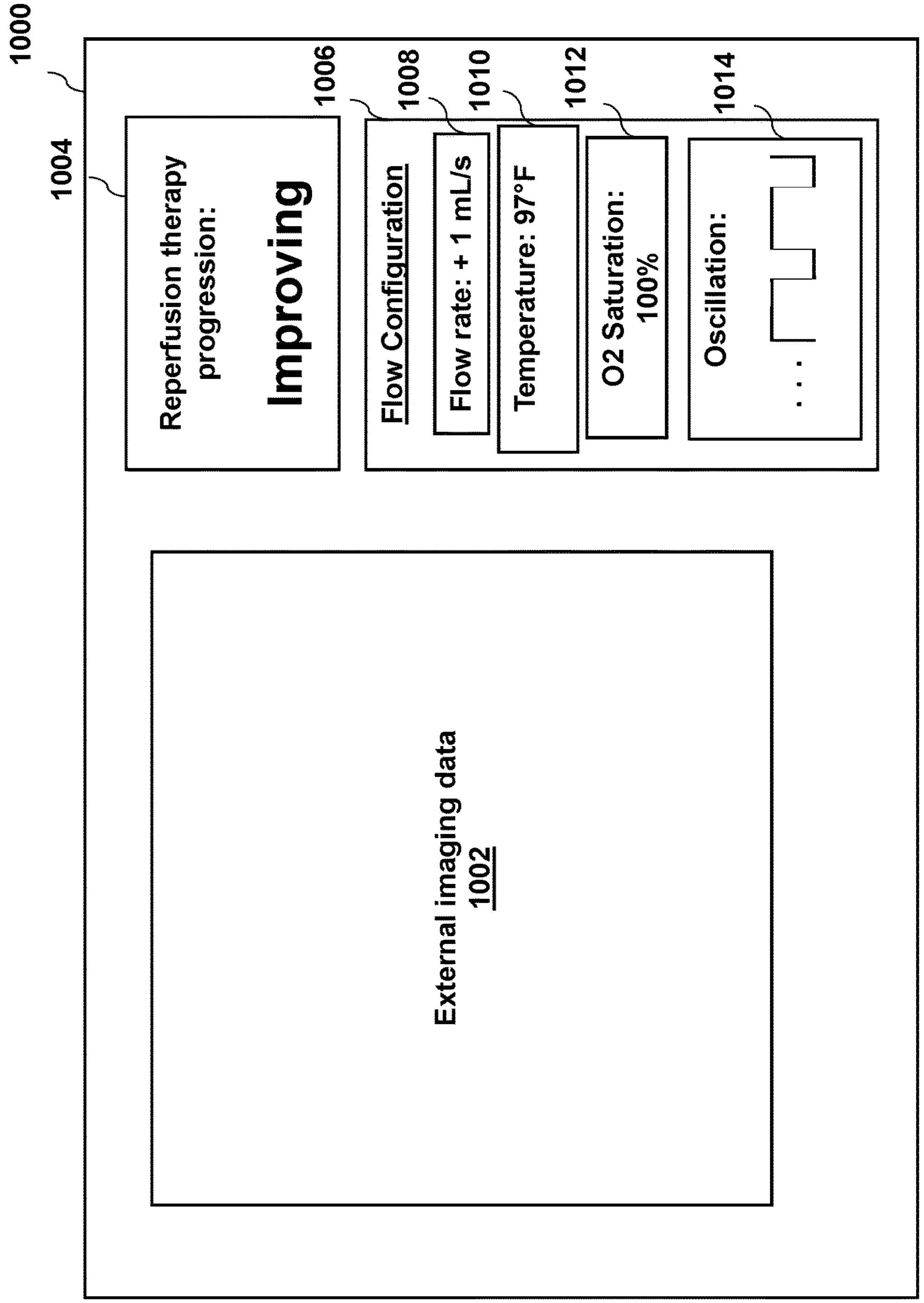
FIG. 10 is a diagrammatic, schematic view of a screen display, in accordance with at least one embodiment of the present disclosure.

FIG. 10 illustrates a screen display 1000, which includes a graphical representation of external imaging data 1002, a visual representation of the progress of the reperfusion therapy 1004, and a visual representation of a flow configuration 1006 (e.g., the flow configuration of fluid under the direction of the intravascular reperfusion therapy device 160). The external imaging data 1002 may be obtained by the external imaging device 140, as described above, and may be output to the display 120 by the processing system 110. The external imaging data 1002 may depict the area of tissue 310, a coronary vein 304 associated with the area of tissue 310 (e.g., the coronary sinus 306), and/or a coronary artery 302 associated with the area of tissue 310. Moreover, the external imaging data 1002 may include contrast in some embodiments. In some embodiments, the delivery and/or progress of a reperfusion therapy may be visualized via the external imaging data 1002.

In some embodiments, the visual representation of the progress of the reperfusion therapy 1004 may include a visual representation of the physiological data and/or a value of a parameter determined based on the physiological data. In that regard, the visual representation may include a representation of blood flow through the blood vessel. In some embodiments, visual representation of the progress of the reperfusion therapy 1004 may include a numerical representation, a graph, chart, or plot, a textual representation, one or more symbols, and/or the like. As further illustrated, in some embodiments, the determined progression of the reperfusion therapy (e.g., at step 804) may be represented textually as a particular status, such as “improving,” “worsening,” “no change,” “complete,” and/or the like. In some embodiments, each status may correspond to a different threshold or range of values of the physiological data, parameters determined based on the data, derivations, external imaging data, and/or the like. For instance, as described above, the status “improving” may correspond to a first range of values for physiological data and/or an associated parameter that correspond to improvement for the area of tissue 310, the status "worsening" may correspond to a second range of values for the physiological data and/or associated parameter that correspond to worsening blood flow conditions associated with the area of tissue 310, the status "no change" may correspond to a third range of values for the physiological data and/or the associated parameter that correspond to the reperfusion therapy demonstrating no effect or a relatively small effect on the area of tissue 310, and the status "complete" may correspond to a fourth range of values for the physiological data and/or the associated parameter that correspond to a healthy level of blood flow associated with the area of tissue 310 and/or to a plateaued maximum value. Further, the progression of the reperfusion therapy may additionally or alternatively be indicated with respective symbols, colors, and/or the like associated with the statuses "improving," "worsening," "no change," "complete," and/or the like. Moreover, the screen display 1000 may include the external imaging data 1002, such as one or more static images or an image stream. In some embodiments, navigating through the static images (e.g., using the input device 130) or watching a progression of the image stream may provide an indication of the progress of the reperfusion therapy, as the visual appearance of contrast delivered to the area of tissue will change based on an impact of the reperfusion therapy.

The visual representation of the flow configuration 1006 may include a visual representation of a flow rate 1008, a visual representation of a temperature 1010, a visual representation of an oxygen saturation level 1012, a visual representation of an oscillation pattern 1014, and/or the like of the fluid controlled (e.g., directed) by the intravascular reperfusion therapy device 160. Each of these visual representations may include may include one or more numerical representations, graphs, charts, plots, textual representations, symbols, and/or the like. The visual representation of the flow rate 1008 may represent the flow rate of fluid moving through the lumen 638 of the intravascular reperfusion therapy device 160. Moreover, the sign of the flow rate may represent the direction of the flow of the fluid. For instance, a positive flow rate may be representative of flow of fluid in a first direction, such as from the lumen 638 into the coronary vein 304, and a negative flow rate may be representative of flow of fluid in an opposite, second direction, such as from the coronary vein 304 into the lumen 638. The visual representation of the temperature 1010 may be representative of the temperature of fluid under the control of the intravascular reperfusion therapy device 160. The temperature may be determined based on one or more sensors in the catheter 634 and/or within the pump, such as within the pump 650. The visual representation of the oxygen saturation level 1012 may be representative of the oxygen saturation of the fluid under the control of the intravascular reperfusion therapy device 160. The oxygen saturation level may be determined based on one or more sensors in the catheter 634 and/or within the pump, such as within the pump 650. The visual representation of the oscillation pattern 1014 may be representative of a pattern (e.g., frequency, duty cycle, duration, and/or the like) used to control the intravascular reperfusion therapy device 160 and, in particular, the pump of the intravascular reperfusion therapy device 160. As illustrated, the visual representation of oscillation pattern 1014 may include a waveform of the oscillation pattern. The oscillation pattern may correspond to a cycling between a first set of operating settings of the pump and a different, second set of operating settings for the pump. The first set of operating settings may control flow of a fluid to a first set of characteristics (e.g., to a first combination of flow velocity, flow rate, flow volume, flow direction, and/or the like), and the second set of operating settings may control flow of a fluid to a different, second set of characteristics (e.g., to a second combination of flow velocity, flow rate, flow volume, flow direction, and/or the like). As an illustrative example, the first set of operating settings may activate the pump to pump fluid, and the second set of operating settings may pause operation of the pump such that the fluid is not actively pumped.

The various visual representation included in the visual representation of the flow configuration 1006 (e.g., 1008, 1010, 1012, 1014) may correspond to a respective set value, such as a value the processing system 110 controlled the intravascular reperfusion therapy device 160 to provide with respect to the fluid, a setting a user selects for the fluid (e.g., via a user input at the input device 130), and/or the like. As an illustrative example, the visual representation of the temperature 1010 may correspond to a temperature of the fluid (e.g., a cooling fluid) delivered for the reperfusion therapy selected by the user (e.g., via the input device 130) for the temperature control unit 662 to produce, which may or may not match the actual or current temperature of the fluid. To that end, the processing system 110 may determine the visual representations of the visual representation of the flow configuration 1006 based on the set values for these characteristics. Additionally or alternatively the visual representation of the flow configuration 1006 may include actual (e.g., sensed) values for different characteristics (e.g., for one or more of the visual representations 1008, 1010, 1012, and/or 1014). For instance, the values may be sensed (e.g., determined and/or measured) by the intravascular reperfusion therapy device 160 (e.g., via the one or more sensors 630, 632, for example), determined based on the external imaging data 1002 (e.g., using image processing techniques, such as pixel level analysis), and/or determined via one or more sensors associated with the pump (e.g., 650 and/or 714). Further, in some embodiments, a visual representation of each of the actual value and the set value of a characteristic (e.g., for one or more of the visual representations 1008, 1010, 1012, and/or 1014) may be output to the display 120.

Based on the visual representation output to the screen display, a user, such as a physician or clinician, may monitor the progression of the reperfusion therapy. Moreover, in some embodiments, the user may also control or modify the reperfusion therapy. For instance, the reperfusion therapy may be further controlled based on one or more user inputs, which may be received via the input device 130, for example. To that end, a user may provide an input at the input device 130, and the processing system 110 may control operation of the intravascular reperfusion therapy device 160 based on the input.

Figure 11:
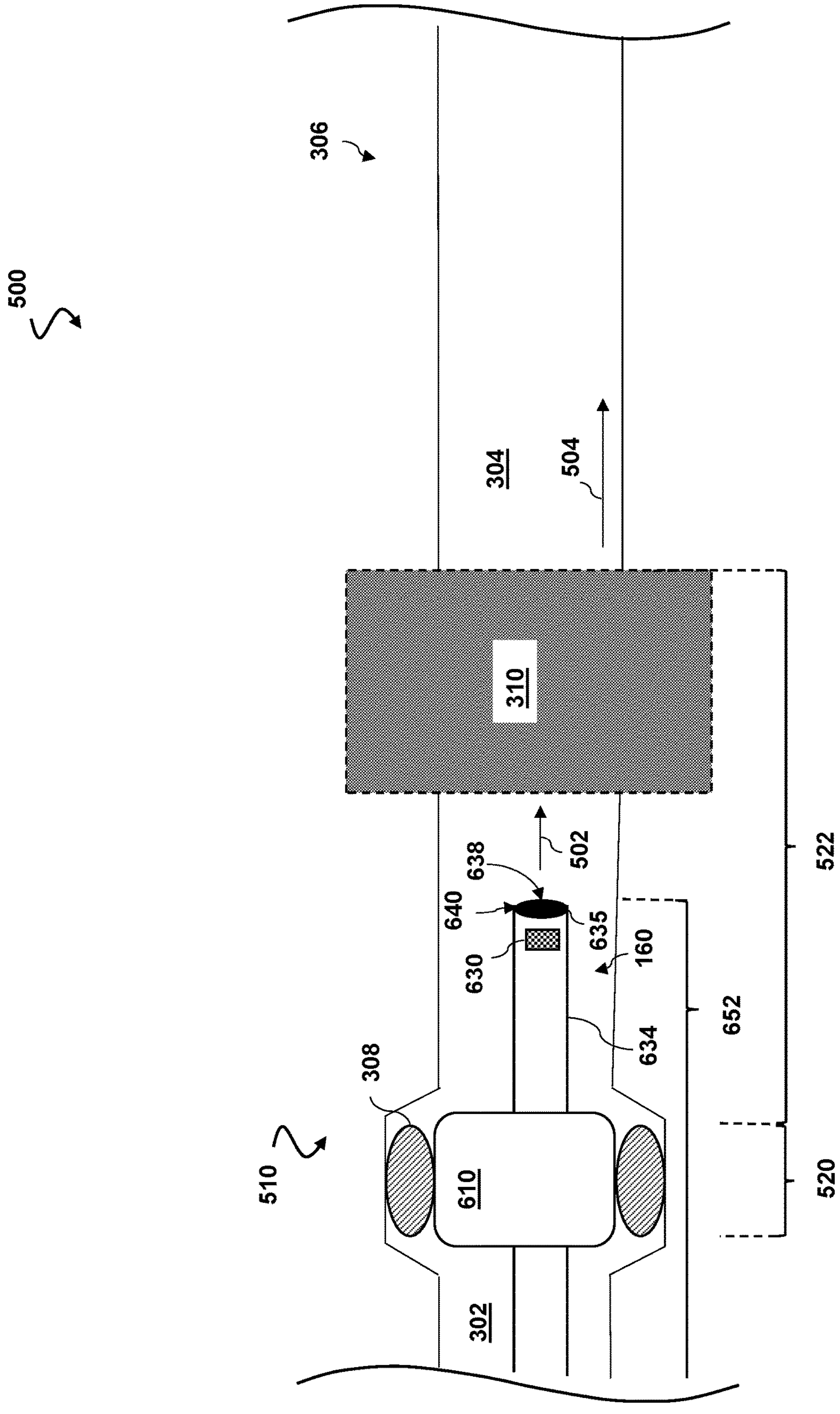
FIG. 11 is a schematic diagram of a portion of a heart, in accordance with at least one embodiment of the present disclosure.

Turning to FIG. 11, a schematic diagram of the portion 500 of the heart during and/or following delivery of a PCI therapy 610 and/or during delivery of a reperfusion therapy is shown. In that regard, FIG. 11, like FIG. 5, may correspond to a detailed view of a portion of the heart 300 illustrated in FIG. 3B. However, while the reperfusion therapy is illustrated in FIG. 5 as being supplied within the venous vasculature (e.g., the coronary sinus 306), the delivery of reperfusion therapy illustrated in FIG. 11 is supplied via the arterial vasculature, such as within the coronary artery 302. In that regard, while the method 800 of FIG. 8 is described with respect to venous delivery of reperfusion therapy, the method 800 may additionally or alternatively be employed with respect to arterial delivery of reperfusion therapy, as described below.

As illustrated in FIG. 11, to deliver reperfusion therapy arterially (e.g., on the arterial side of the area of tissue 310), the intravascular reperfusion therapy device 160 may be positioned within the coronary artery 302. In particular, the intravascular reperfusion therapy device 160 may be positioned such that one or more sensors (e.g., the first sensor 630 and/or the second sensor 710) of the device 160 are disposed distal of the blockage 308 (e.g., within the distal area 522). In that regard, the processing system 110 may receive physiological data associated with blood flow through a portion of the coronary artery 302 distal of the blockage 308 (e.g., distal area 522) at step 802 of the method 800 (FIG. 8). Further, because characteristics of the blood flow through the coronary artery 302 may vary in comparison with the blood flow through the coronary veins 304, the physiological data and/or parameters associated with blood flow derived from the physiological data may be compared against different thresholds or otherwise related to a progression of a reperfusion therapy (e.g., at step 804 of the method 800) differently than the corresponding data during venous reperfusion therapy. In general, reperfusion therapy targeting the area of tissue 310 may increase blood flow through the area of tissue 310 by, for example, reducing resistance and/or impedance to flow within the area of tissue 310. Accordingly, physiological data demonstrating that blood flow through the area of tissue 310 is increasing may indicate a progression of a reperfusion therapy that is effective and/or achieving an intended effect, while physiological data demonstrating that blood flow through the area of tissue 310 is decreasing or unchanging may indicate a progression of a reperfusion therapy that is effective and/or achieving an intended effect.

The intravascular reperfusion therapy device 160 may be the same as or different from the intravascular lesion therapy device 150. In that regard, the intravascular reperfusion therapy device 160 may be configured to deliver the reperfusion therapy after a PCI therapy 610 is delivered and/or the intravascular reperfusion therapy device 160 may deliver both the PCI therapy 610 as well as reperfusion therapy. As an illustrative example, the catheter 634 may be used to deploy a stent and/or perform angioplasty (e.g., the PCI therapy 610) and may subsequently be used to deliver reperfusion therapy. In that regard, to deliver the reperfusion therapy, the intravascular reperfusion therapy device 160 may be co-located with the blockage 308 and/or the site where the PCI therapy 610 is delivered. In some embodiments, the intravascular reperfusion therapy device 160 or a portion thereof, such as the distal end 640, may be positioned between the portion 520 of the vessel where the blockage 308 and/or PCI therapy 610 (e.g., a stent) is located and the area of tissue 310. That is, for example, the distal end 640 may be positioned distal of the blockage 308 and/or the PCI therapy 610 (e.g., a stent) (e.g., within the distal area 522), as illustrated. Additionally or alternatively, the distal end 640 may be positioned proximal of the portion 520 of the vessel where the blockage 308 and/or PCI therapy 610 (e.g., a stent) is located.

In cases where the reperfusion therapy is delivered arterially, the intravascular reperfusion therapy device 160 may be configured to deliver cooling fluid and/or super-oxygenated fluid. As described above, delivery of cooling fluid, which, at least when delivered arterially, may flow into the area of tissue 310 (e.g., in the direction indicated by arrow 502), may reduce inflammation in the area of tissue 310. By reducing the inflammation within the area of tissue 310 blood flow may increase and/or may better distribute throughout the area of tissue 310, reducing or preventing reperfusion injury. Further, delivery of super-oxygenated fluid may increase the likelihood that portions of the area of tissue 310 receive oxygen. In this regard, delivery of the super-oxygenated fluid to the area of tissue may also reduce or prevent reperfusion injury.

In some cases, arterial delivery of reperfusion therapy may additionally or alternatively involve a controlled and/or increase in blood flow to the area of tissue following the PCI therapy 610. In some embodiments, for example, gradually increasing blood flow through the tissue 310 may minimize or prevent reperfusion injury from occurring and/or may reverse an effect of reperfusion injury. In that regard, in cases where the intravascular reperfusion therapy device 160 is used to deliver the reperfusion therapy arterially, the processing system 110 may control the intravascular reperfusion therapy device 160 to gradually reintroduce blood flow to the tissue 310. In some cases, for example, the processing system may control the intravascular reperfusion therapy device 160 such that the intravascular reperfusion therapy device 160 diverts (e.g., pumps blood into the lumen 638) a volume of blood in the coronary artery 302 for a certain duration and may then reduce the diverted volume to increase the volume of blood provided to the area of tissue 310. Additionally or alternatively, the processing system 110 may control the intravascular reperfusion therapy device 160 to provide fluid (e.g., via the lumen 638) to the coronary artery 302 (e.g., in the direction indicated by arrow 502). In particular, the processing system 110 may control the intravascular reperfusion therapy device 160 to gradually increase the flow rate, flow volume, and/or flow velocity of fluid delivered to the coronary artery to control the increase in fluid flow provided to the area of tissue 310. Mechanisms to adjust reperfusion therapies described herein are intended to be illustrative and not limiting.

Figure 12B:
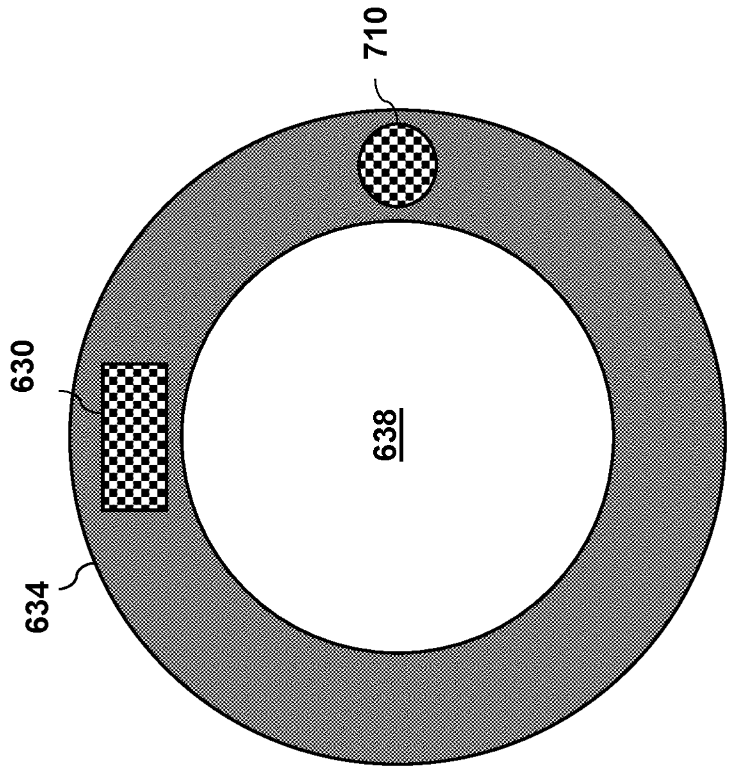
FIG. 12B is a front view of an intravascular reperfusion therapy device, in accordance with at least one embodiment of the present disclosure.
Figure 12A:
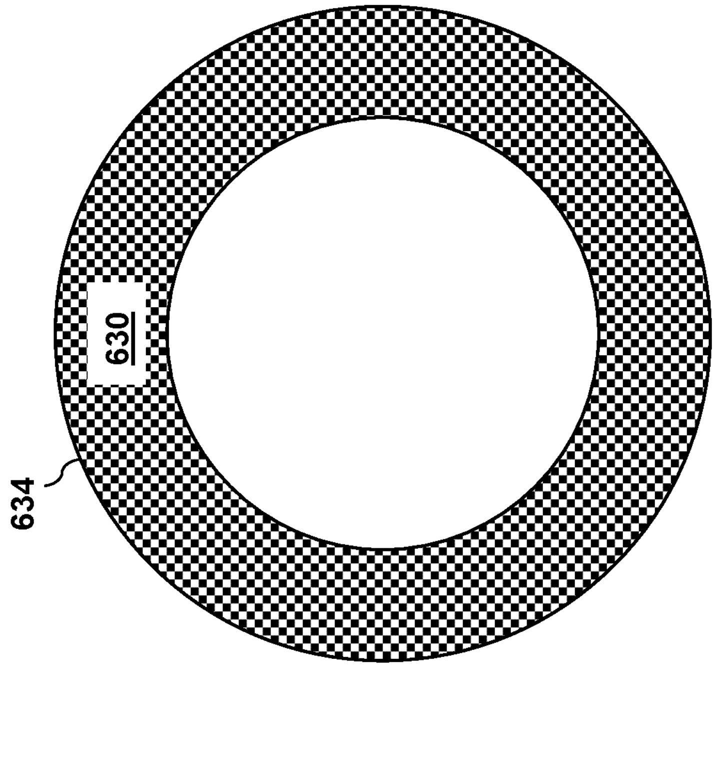
FIG. 12A is a front view of an intravascular reperfusion therapy device, in accordance with at least one embodiment of the present disclosure.

FIGS. 12A-12B illustrate exemplary arrangements of the one or more sensors (e.g., first sensor 630 and/or second sensor 710) of the intravascular reperfusion therapy device 160. In particular, FIGS. 12A-12B illustrate a front view of a cross section of a catheter 634 of the intravascular reperfusion therapy device 160. In an exemplary embodiment, FIG. 12A illustrates a front view of the first sensor 630 positioned on a distal end 640 of the catheter 634, where the catheter 634 terminates. In other embodiments, the first sensor 630 and the illustrated cross section of FIG. 12A may be spaced from the distal end of the catheter. To that end, FIG. 12A may be representative of the arrangement of the second sensor 710 in a cross section of the catheter 634 proximal of the distal end 640. Further, in an exemplary embodiment, FIG. 12B illustrates a front view of the first sensor 630 and the second sensor 710 positioned on a distal end of the catheter 634. In other embodiments, the first sensor 630, the second sensor 710, and the illustrated cross section may be spaced from the distal end of the catheter 634. Moreover, while FIGS. 12A-12B are illustrated and described with respect to positioning of sensors on a catheter, embodiments are not limited thereto. In that regard, the illustrated sensors may additionally or alternatively be arranged on a guidewire according to the techniques described herein.

In some embodiments, the one or more sensors of the intravascular reperfusion therapy device 160 may include one or more transducers, such as one or more ultrasound transducer elements. To that end, the illustrated configurations of FIGS. 12A-12B may be representative of one or more transducers. The one or more ultrasound transducer elements (e.g., acoustic elements) may be configured to emit ultrasound energy and receive echoes corresponding to the emitted ultrasound energy. Further, the one or more ultrasound transducer elements may include a piezoelectric/piezoresistive element, a piezoelectric micromachined ultrasound transducer (PMUT) element, a capacitive micromachined ultrasound transducer (CMUT) element, and/or any other suitable type of ultrasound transducer element. The one or more ultrasound transducer elements may further be in communication with (e.g., electrically coupled to) electronic circuitry. For example, the electronic circuitry can include one or more transducer control logic dies. The electronic circuitry can include one or more integrated circuits (IC), such as application specific integrated circuits (ASICs). In some embodiments, one or more of the ICs can include a microbeamformer (μBF). In other embodiments, one or more of the ICs includes a multiplexer circuit (MUX).

Further the one or more transducers of the one or more sensors may be arranged in any suitable configuration. For example, the transducers may be positioned in an array of ultrasound transducer elements, such as a linear array, a planar array, a curved array, a curvilinear array, a circumferential array, an annular array, a phased array, a matrix array, a one-dimensional (1D) array, a 1.x dimensional array (e.g., a 1.5D array), or a two-dimensional (2D) array. The array of transducer elements (e.g., one or more rows, one or more columns, and/or one or more orientations) can be uniformly or independently controlled and activated. The array can be configured to obtain one-dimensional, two-dimensional, and/or three-dimensional images of patient anatomy.

In an exemplary embodiment, the first sensor 630 or the second sensor 710 is a flow sensor, which includes a single ultrasound transducer element, such as the transducer elements described above. The transducer element emits ultrasound signals and receives ultrasound echoes reflected from anatomy (e.g., flowing fluid, such as blood). The transducer element generates electrical signals representative of the echoes. These electrical signals are carried from the sensor at the distal portion 652 of the device 160 to a connector at the proximal portion of the device 160, which may be communicatively coupled to the processing system 110. The processing system 110 can then process the electrical signals to extract the flow velocity of the fluid.

In some embodiments, the first sensor 630 or the second sensor 710 is thermal anemometric sensor, such as a thermal anemometric flow sensor. In such cases, the sensor may be maintained at a relatively constant temperature, and the electrical power consumed to maintain this temperature as blood flows proximate the sensor may be sensed and as representative of the flow velocity of the blood flow. Alternatively, a relatively constant power may be supplied to the sensor, and a change in temperature of the sensor as the blood flows proximate the sensor may be sensed as representative of the flow velocity of the blood flow. For instance, the processing system 110 may relate the consumed power or the temperature change, respectively to determine the flow velocity of the blood. While the sensors are described as being implemented with transducer elements or as a thermal anemometric sensor, embodiments are not limited thereto. In that regard, any suitable sensor configured to obtain physiological data associated with blood flow may be utilized in the intravascular reperfusion therapy device 160.

As shown in FIG. 12A, the first sensor 630 is arranged in an annular configuration about (e.g., following an outer perimeter of) the catheter 634. This annular configuration may include one or more transducers, such as one or more ultrasound transducers, as described above. Further, in some embodiments, the transducer elements and/or the sensor 630 may be forward-facing. That is, for example, the first sensor 630 may be a flow sensor arranged so that the first sensor 630 senses (e.g., emits signals) along the axis blood flows along within the vessel (e.g., the axis including the blood flow directions indicated by arrow 502 and arrow 504 in FIGS. 4-5, 9, and 11), which may correspond to the longitudinal axis of the intravascular reperfusion therapy device). In that regard, the first sensor 630 may be arranged to sense in a direction aligned with or opposite the direction of blood flow within the vessel. In some embodiments, the sensor 630 may be substantially perpendicular with the longitudinal axis of the intravascular reperfusion therapy device 160 to be forward-facing. In some embodiments, the sensor 630 may be positioned at an oblique angle (e.g., tilted) such that at least a portion of the signals emitted by the sensor 630 detect physiological data with respect to the axis that blood flows along within the vessel. For instance, in cases where the first sensor 630 is spaced from the distal end of the intravascular reperfusion therapy device 160, the first sensor 630 may be positioned at an angle to detect blood flow.

FIG. 12B, illustrates the first sensor 630 and a second sensor 710 positioned on the catheter 634. Again, the illustrated first sensor 630 may represent one or more transducers, and the illustrated second sensor 710 may represent one or more transducers. Moreover, the first sensor 630 and the second sensor 710 may be the same or different. For instance, the first sensor 630 may be a flow sensor, as described above, and the second sensor 710 may be a flow sensor or a pressure sensor.

In some embodiments, the first sensor 630 and the second sensor 710 may be spaced from one another along the circumference of the catheter 634, as illustrated. Further, the first sensor 630 and the second sensor 710 may face the same or different directions. For instance, the first sensor 630 may be entirely forward facing (e.g., perpendicular to the longitudinal axis of the device 160), while the second sensor 710 may be tilted or parallel with the axis of the device 160. The second sensor 710 may be a pressure sensor arranged parallel with the axis of the device 160, for example.

Further, in some embodiments, the first sensor 630 and the second sensor 710 may be positioned within the catheter 634, such as within the lumen 638 of the catheter 634 and/or within a housing positioned within or defined by the lumen 638. In some embodiments, the first sensor 630 and the second sensor 710 may be embedded within a material of the catheter 634 or positioned on an outer surface of the catheter 634. In that regard, the first sensor 630 and the second sensor 710 may be arranged in any suitable configuration for collecting physiological data intravascularly. Additionally or alternatively, the first sensor 630 and/or the second sensor 710 may be arranged to collect data representative of flow of fluid within the lumen 638. That is, for example, the first sensor 630 and/or the second sensor 710 may sense one or more parameters within the intravascular reperfusion therapy device 160 itself.

While the system 100 and the method 800 are described herein as being employed for evaluating (e.g., assessing) and/or controlling reperfusion therapy, embodiments are not limited thereto. In that regard, the techniques described herein may additionally or alternatively be applied to microvascular disease (e.g., affecting capillary beds, for example) in any portion of a patient's anatomy (e.g., within or separate from the heart) and/or to nonobstructive coronary artery disease. Moreover, assessment and/or control of blood flow through particular tissue and/or capillary beds may be performed with or without a PCI therapy being performed on a vessel associated with the tissue and/or capillary beds.

A person of ordinary skill in the art will recognize that the present disclosure advantageously provides a system and method suitable to evaluate (e.g., assess) and control (e.g., adjust) a reperfusion therapy associated with an area of tissue. In particular, the techniques described herein enable adaptive delivery of a reperfusion therapy via intravascular fluid delivery based on sensed physiological data. The logical operations making up the embodiments of the technology described herein are referred to variously as operations, steps, objects, elements, components, regions, etc. Furthermore, it should be understood that these may occur in any order, unless explicitly claimed otherwise or a specific order is inherently necessitated by the claim language.

It should further be understood that the described technology may be employed in a variety of different applications, including but not limited to human medicine, veterinary medicine, education and inspection. All directional references e.g., upper, lower, inner, outer, upward, downward, left, right, lateral, front, back, top, bottom, above, below, vertical, horizontal, clockwise, counterclockwise, proximal, and distal are only used for identification purposes to aid the reader's understanding of the claimed subject matter, and do not create limitations, particularly as to the position, orientation, or use of the intraluminal imaging system. Connection references, e.g., attached, coupled, connected, and joined are to be construed broadly and may include intermediate members between a collection of elements and relative movement between elements unless otherwise indicated. As such, connection references do not necessarily imply that two elements are directly connected and in fixed relation to each other. The term "or" shall be interpreted to mean "and/or" rather than "exclusive or." The word "comprising" does not exclude other elements or steps, and the indefinite article "a" or "an" does not exclude a plurality. Unless otherwise noted in the claims, stated values shall be interpreted as illustrative only and shall not be taken to be limiting.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A system, comprising:

an intravascular reperfusion therapy device configured to be positioned within a coronary vein of a patient to deliver reperfusion therapy to a myocardium of a heart of the patient associated with the coronary vein, wherein the intravascular reperfusion therapy device comprises a sensor, a pump, and a catheter comprising a lumen, wherein the intravascular reperfusion therapy device is configured to, using the pump, direct flow of a fluid through the lumen to deliver the reperfusion therapy; and a processor circuit in communication with the intravascular reperfusion therapy device and configured to:

receive, from the sensor, physiological data associated with blood flow through the coronary vein;

determine, based on the physiological data, a progression of the reperfusion therapy delivered to the myocardium of the heart, wherein the progression of the reperfusion therapy comprises a plurality of states indicative of an effect of the reperfusion therapy on the myocardium, wherein the plurality of states respectively correspond to different values of the physiological data; and control, based on the progression of the reperfusion therapy, the flow of the fluid through the lumen such that the reperfusion therapy is controlled.

2. The system of claim 1, wherein, to control the flow of the fluid through the lumen, the processor circuit is configured to:

control, via the pump, a flow rate of the flow of the fluid through the lumen.

3. The system of claim 1, wherein, to control the flow of the fluid through the lumen, the processor circuit is configured to:

control, via the pump, a direction of the flow of the fluid through the lumen.

4. The system of claim 3, wherein, to control the direction of the flow of the fluid through the lumen, the processor circuit is configured to control the intravascular reperfusion therapy device to, using the pump:

deliver the fluid from the lumen to the coronary vein to generate a back pressure in a first direction, wherein the first direction is opposite a second direction of the blood flow through the coronary vein; or receive the fluid from the coronary vein via the lumen to reduce a pressure in the coronary vein.

5. The system of claim 1, wherein, to control the flow of the fluid through the lumen, the processor circuit is configured to:

control the intravascular reperfusion therapy device to, using the pump, oscillate a direction of the flow of the fluid through the lumen between a first direction and a different, second direction.

6. The system of claim 1, wherein the intravascular reperfusion therapy device is further configured to control a temperature of the fluid to deliver the reperfusion therapy, wherein, based on the progression of the reperfusion therapy, the processor circuit is further configured to: control the intravascular reperfusion therapy device to control the temperature of the fluid such that temperature of the myocardium is controlled.

7. The system of claim 1, wherein the intravascular reperfusion therapy device is further configured to control an oxygen saturation level in the fluid to deliver the reperfusion therapy, wherein, based on the progression of the reperfusion therapy, the processor circuit is further configured to: control the intravascular reperfusion therapy device to control the oxygen saturation level in the fluid.

8. The system of claim 1, wherein the pump is coupled to the catheter and is configured to be positioned within a blood vessel of the patient.

9. The system of claim 8, wherein the intravascular reperfusion therapy device comprises a first port proximal of the pump and a second port distal of the pump, wherein the first port, the second port, and the pump are in fluid communication with the lumen.

10. The system of claim 9, wherein, to direct the flow of the fluid through the lumen, the intravascular reperfusion therapy device is configured to control the pump to:

intake the fluid via the first port and output the fluid via the second port such that the fluid flows through the lumen in a first direction; or intake the fluid via the second port and output the fluid via the first port such that the fluid flows through the lumen in a different, second direction.

11. The system of claim 1, wherein the pump is positioned external to the patient.

12. The system of claim 1, wherein the sensor is positioned at a distal portion of the catheter.

13. The system of claim 1, wherein the intravascular reperfusion therapy device comprises an additional sensor, wherein the processor circuit is further configured to:

receive, from the additional sensor, additional physiological data associated with blood flow through the coronary vein, wherein the processor circuit is configured to determine the progression of the reperfusion therapy further based on the additional physiological data.

14. The system of claim 1, wherein the fluid comprises at least one of saline or blood.

15. The system of claim 1, wherein the processor circuit is further configured to:

output, to display in communication with the processor circuit, a visual representation of the progression of the reperfusion therapy.

16. The system of claim 1, wherein the sensor comprises a flow sensor, wherein the physiological data comprises a blood flow rate.

17. The system of claim 1, wherein the sensor comprises a pressure sensor, wherein the physiological data comprises pressure data.

18. The system of claim 1, wherein the plurality of states comprises two or more of: improving, worsening, no change, or complete.

19. A system, comprising:

an intravascular reperfusion therapy device configured to be positioned within a coronary vein of a patient to deliver reperfusion therapy to a myocardium of a heart of the patient associated with the coronary vein, wherein the intravascular reperfusion therapy device comprises:

a catheter comprising a lumen;

a flow sensor positioned at a distal portion of the catheter; and a pump in fluid communication with the lumen, wherein the intravascular reperfusion therapy device is configured to deliver the reperfusion therapy by, using the pump, directing flow of a fluid through the lumen to the coronary vein in a first direction to generate back pressure in an opposite, second direction within the coronary vein; and a processor circuit in communication with the intravascular reperfusion therapy device and configured to:

receive, from the flow sensor, flow data associated with blood flow through the coronary vein;

determine, based on the flow data, a progression of the reperfusion therapy delivered to the myocardium of the heart, wherein the progression of the reperfusion therapy comprises a plurality of states indicative of an effect of the reperfusion therapy on the myocardium, wherein the plurality of states respectively correspond to different values of the flow data; and control, based on the progression of the reperfusion therapy, the flow of the fluid through the lumen such that the back pressure within the coronary vein is controlled.

* * * * *